(12) United States Patent
Burton et al.

(10) Patent No.: US 10,881,106 B2
(45) Date of Patent: Jan. 5, 2021

(54) HERBICIDAL PYRIDAZINONE COMPOUNDS

(71) Applicant: SYNGENTA PARTICIPATIONS AG, Basel (CH)

(72) Inventors: Paul Matthew Burton, Bracknell (GB); Edward John Emmett, Bracknell (GB); Alexander Martin Richard Smith, Bracknell (GB); Louisa Whalley, Bracknell (GB)

(73) Assignee: SYNGENTA PARTICIPATIONS AG, Basel (CH)

( * ) Notice: Subject to any disclaimer, the term of this patent is extended or adjusted under 35 U.S.C. 154(b) by 67 days.

(21) Appl. No.: 16/345,722

(22) PCT Filed: Oct. 24, 2017

(86) PCT No.: PCT/EP2017/077158
§ 371 (c)(1),
(2) Date: Apr. 28, 2019

(87) PCT Pub. No.: WO2018/077875
PCT Pub. Date: May 3, 2018

(65) Prior Publication Data
US 2020/0054012 A1 Feb. 20, 2020

(30) Foreign Application Priority Data
Oct. 28, 2016 (GB) .................................. 1618266.9

(51) Int. Cl.
*A01N 43/58* (2006.01)
*A01N 43/84* (2006.01)
*C07D 237/14* (2006.01)

(52) U.S. Cl.
CPC ............. *A01N 43/58* (2013.01); *A01N 43/84* (2013.01); *C07D 237/14* (2013.01)

(58) Field of Classification Search
None
See application file for complete search history.

(56) References Cited

FOREIGN PATENT DOCUMENTS

WO 201236703 A1 10/2012

OTHER PUBLICATIONS

International Search Report issued by EPO dated Dec. 19, 2017.

*Primary Examiner* — Alton N Pryor
(74) *Attorney, Agent, or Firm* — Baker & Hostetler LLP; Toni-Junell Herbert

(57) ABSTRACT

The present invention relates to compounds of Formula (I), or an agronomically acceptable salt of said compounds wherein $R^{1a}$, $R^{1b}$, $R^2$, X, A, $R^a$, $R^b$, $R^c$, $R^d$ and m are as defined herein. The invention further relates to herbicidal compositions which comprise a compound of Formula (I), to their use for controlling weeds. The invention further relates to intermediate compounds used to produce compounds of Formula (I).

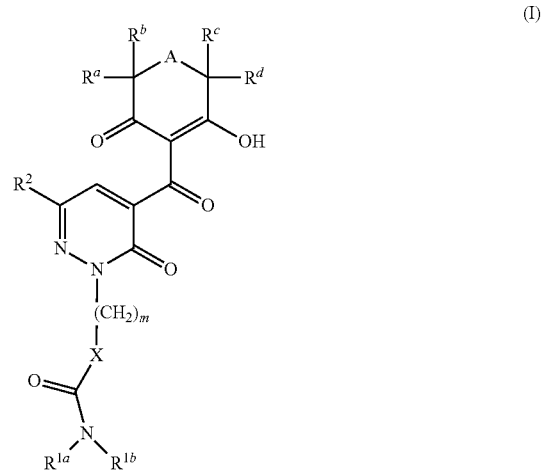

15 Claims, No Drawings

HERBICIDAL PYRIDAZINONE COMPOUNDS

CROSS-REFERENCE TO RELATED APPLICATIONS

This application is a 371 National Stage application of International Application No. PCT/EP2017/077158, filed Oct. 24, 2017, which claims priority to European Application No. 1618266.9 filed Oct. 28, 2016, the entire contents of which applications are hereby incorporated by reference.

The present invention relates to novel herbicidal compounds, to herbicidal compositions which comprise the novel compounds, and to their use in controlling weeds.

Herbicidal pyridazinone derivatives are disclosed in WO2012/136703. The present invention relates to novel herbicidal pyridazinone derivatives, which are shown to exhibit improved crop selectivity.

Thus, according to the present invention there is provided a compound of Formula (I):

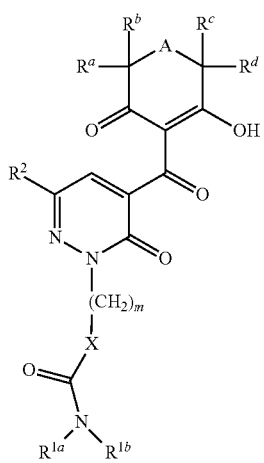

or an agronomically acceptable salt thereof,
wherein:—
$R^{1a}$ is selected from the group consisting of hydrogen, $C_1$-$C_6$alkyl and $C_1$-$C_6$haloalkyl;
$R^{1b}$ is selected from the group consisting of hydrogen, $C_1$-$C_6$alkyl, $C_1$-$C_3$alkoxy- and $C_1$-$C_6$haloalkyl; or
$R^{1a}$ and $R^{1b}$ together are —$CH_2CH_2CH_2CH_2$—, —$CH_2CH_2CH_2CH_2CH_2$— or —$CH_2CH_2OCH_2CH_2$—; and
X is selected from the group consisting of O, —$CF_2$—, —$C(CH_3)$— and —$CH_2$—;
m is 0, 1 or 2 wherein if X is O or —$CF_2$— then m is 1 or 2;
$R^2$ is selected from the group consisting of hydrogen, $C_1$-$C_6$alkyl and $C_3$-$C_6$cycloalkyl;
$A^1$ is selected from the group consisting of O, C(O) and (CR$^e$R$^f$); and
$R^a$, $R^b$, $R^c$, $R^d$, $R^e$ and $R^f$ are each independently selected from the group consisting of hydrogen and $C_1$-$C_4$alkyl wherein $R^a$ and $R^c$ may together form a $C_1$-$C_3$alkylene chain.

The term $C_1$-$C_6$alkyl and $C_1$-$C_4$alkyl groups include, for example, methyl (Me, $CH_3$), ethyl (Et, $C_2H_5$), n-propyl (n-Pr), isopropyl (i-Pr), n-butyl (n-Bu), isobutyl (i-Bu), sec-butyl and tert-butyl (t-Bu).

The term $C_1$-$C_6$haloalkyl includes, for example, fluoromethyl-, difluoromethyl-, trifluoromethyl-, chloromethyl-, dichloromethyl-, trichloromethyl-, 2,2,2-trifluoroethyl-, 2-fluoroethyl-, 2-chloroethyl-, pentafluoroethyl-, 1,1-difluoro-2,2,2-trichloroethyl-, 2,2,3,3-tetrafluoroethyl-, 2,2,2-trichloroethyl-, heptafluoro-n-propyl and perfluoro-n-hexyl. $C_1$-$C_4$haloalkyl includes, for example, fluoromethyl-, difluoromethyl-, trifluoromethyl-, chloromethyl-, dichloromethyl-, trichloromethyl-, 2,2,2-trifluoroethyl-, 2-fluoroethyl-, 2-chloroethyl-, pentafluoroethyl-, 1,1-difluoro-2,2,2-trichloroethyl-, 2,2,3,3-tetrafluoroethyl-, 2,2,2-trichloroethyl- and heptafluoro-n-propyl-.

The term $C_1$-$C_3$alkoxy includes, for example, methoxy (MeO—) and ethoxy-(EtO—).

The term $C_3$-$C_6$cycloalkyl includes cyclopropyl (cPr), cyclobutyl (cBu), cyclopentyl and cyclohexyl.

The term $C_1$-$C_3$alkylene chain includes methylene (—$CH_2$—), ethylene (—$CH_2$—$CH_2$—) and propylene (—$CH_2$—$CH_2$—$CH_2$—).

In one embodiment of the present invention X is selected from the group consisting of O, —$CF_2$— and —$CH_2$—.

In a further embodiment of the present invention, X is oxygen (O). In another embodiment, X is —$CH_2$—.

In a preferred embodiment of the present invention, $R^2$ is $C_1$-$C_6$alkyl, preferably methyl.

In another preferred embodiment of the present invention, $R^{1a}$ is hydrogen and $R^{1b}$ is $C_1$-$C_6$alkyl.

In another preferred embodiment of the present invention, $R^{1a}$ and $R^{1b}$ are both $C_1$-$C_6$alkyl (preferably methyl or ethyl).

In another embodiment of the present invention $A^1$ is (CR$^e$R$^f$). In this instance, a preferred embodiment is wherein $R^a$, $R^b$, $R^c$, $R^d$, $R^e$ and $R^f$ are hydrogen. In another preferred embodiment $R^a$, $R^b$, $R^c$, $R^d$, $R^e$ are hydrogen and $R^f$ is methyl. In another preferred embodiment $R^a$, $R^b$, $R^c$, $R^d$ are hydrogen and $R^e$ and $R^f$ are methyl. In another preferred embodiment $R^b$, $R^d$, $R^e$, and $R^f$ are hydrogen and $R^a$ and $R^c$ form an ethylene chain.

Compounds of Formula (I) (and certain intermediate compounds used to synthesise compound of Formula (I)) may contain asymmetric centres and may be present as a single enantiomer, pairs of enantiomers in any proportion or, where more than one asymmetric centre are present, contain diastereoisomers in all possible ratios. Typically one of the enantiomers has enhanced biological activity compared to the other possibilities.

Similarly, where there are disubstituted alkenes, these may be present in E or Z form or as mixtures of both in any proportion.

Furthermore, compounds of Formula (I) may be in equilibrium with alternative tautomeric forms. It should be appreciated that all tautomeric forms (single tautomer or mixtures thereof), racemic mixtures and single isomers are included within the scope of the present invention.

The present invention also includes agronomically acceptable salts that the compounds of Formula (I). Salts that the compounds of Formula (I) may form with amines, including primary, secondary and tertiary amines (for example ammonia, dimethylamine and triethylamine), alkali metal and alkaline earth metal bases, transition metals or quaternary ammonium bases are preferred. Aluminium, calcium, cobalt, copper (copper (I), copper (II)), iron (iron (II), iron (III)), magnesium, potassium, sodium or zinc salts of compounds of Formula (I) are particularly preferred, copper, potassium and sodium being especially preferred.

The compounds of Formula (I) according to the invention can be used as herbicides by themselves, but they are generally formulated into herbicidal compositions using formulation adjuvants, such as carriers, solvents and surface-active agents (SFAs). Thus, the present invention further provides a herbicidal composition comprising a herbicidal compound of the present invention and an agriculturally acceptable formulation adjuvant. The composition can be in the form of concentrates which are diluted prior to use, although ready-to-use compositions can also be made. The final dilution is usually made with water, but can be made instead of, or in addition to, water, with, for example, liquid fertilisers, micronutrients, biological organisms, oil or solvents.

The herbicidal compositions generally comprise from 0.1 to 99% by weight, especially from 0.1 to 95% by weight, compounds of Formula I and from 1 to 99.9% by weight of a formulation adjuvant which preferably includes from 0 to 25% by weight of a surface-active substance.

The compositions can be chosen from a number of formulation types, many of which are known from the Manual on Development and Use of FAO Specifications for Plant Protection Products, 5th Edition, 1999. These include dustable powders (DP), soluble powders (SP), water soluble granules (SG), water dispersible granules (WG), wettable powders (WP), granules (GR) (slow or fast release), soluble concentrates (SL), oil miscible liquids (OL), ultra low volume liquids (UL), emulsifiable concentrates (EC), dispersible concentrates (DC), emulsions (both oil in water (EW) and water in oil (EO)), micro-emulsions (ME), suspension concentrates (SC), aerosols, capsule suspensions (CS) and seed treatment formulations. The formulation type chosen in any instance will depend upon the particular purpose envisaged and the physical, chemical and biological properties of the compound of Formula (I).

Dustable powders (DP) may be prepared by mixing a compound of Formula (I) with one or more solid diluents (for example natural clays, kaolin, pyrophyllite, bentonite, alumina, montmorillonite, kieselguhr, chalk, diatomaceous earths, calcium phosphates, calcium and magnesium carbonates, sulphur, lime, flours, talc and other organic and inorganic solid carriers) and mechanically grinding the mixture to a fine powder.

Soluble powders (SP) may be prepared by mixing a compound of Formula (I) with one or more water-soluble inorganic salts (such as sodium bicarbonate, sodium carbonate or magnesium sulphate) or one or more water-soluble organic solids (such as a polysaccharide) and, optionally, one or more wetting agents, one or more dispersing agents or a mixture of said agents to improve water dispersibility/solubility. The mixture is then ground to a fine powder. Similar compositions may also be granulated to form water soluble granules (SG).

Wettable powders (WP) may be prepared by mixing a compound of Formula (I) with one or more solid diluents or carriers, one or more wetting agents and, preferably, one or more dispersing agents and, optionally, one or more suspending agents to facilitate the dispersion in liquids. The mixture is then ground to a fine powder. Similar compositions may also be granulated to form water dispersible granules (WG).

Granules (GR) may be formed either by granulating a mixture of a compound of Formula (I) and one or more powdered solid diluents or carriers, or from pre-formed blank granules by absorbing a compound of Formula (I) (or a solution thereof, in a suitable agent) in a porous granular material (such as pumice, attapulgite clays, fuller's earth, kieselguhr, diatomaceous earths or ground corn cobs) or by adsorbing a compound of Formula (I) (or a solution thereof, in a suitable agent) on to a hard core material (such as sands, silicates, mineral carbonates, sulphates or phosphates) and drying if necessary. Agents which are commonly used to aid absorption or adsorption include solvents (such as aliphatic and aromatic petroleum solvents, alcohols, ethers, ketones and esters) and sticking agents (such as polyvinyl acetates, polyvinyl alcohols, dextrins, sugars and vegetable oils). One or more other additives may also be included in granules (for example an emulsifying agent, wetting agent or dispersing agent).

Dispersible Concentrates (DC) may be prepared by dissolving a compound of Formula (I) in water or an organic solvent, such as a ketone, alcohol or glycol ether. These solutions may contain a surface active agent (for example to improve water dilution or prevent crystallisation in a spray tank).

Emulsifiable concentrates (EC) or oil-in-water emulsions (EW) may be prepared by dissolving a compound of Formula (I) in an organic solvent (optionally containing one or more wetting agents, one or more emulsifying agents or a mixture of said agents). Suitable organic solvents for use in ECs include aromatic hydrocarbons (such as alkylbenzenes or alkylnaphthalenes, exemplified by SOLVESSO 100, SOLVESSO 150 and SOLVESSO 200; SOLVESSO is a Registered Trade Mark), ketones (such as cyclohexanone or methylcyclohexanone) and alcohols (such as benzyl alcohol, furfuryl alcohol or butanol), N-alkylpyrrolidones (such as N-methylpyrrolidone or N-octylpyrrolidone), dimethyl amides of fatty acids (such as $C_8$-$C_{10}$ fatty acid dimethylamide) and chlorinated hydrocarbons. An EC product may spontaneously emulsify on addition to water, to produce an emulsion with sufficient stability to allow spray application through appropriate equipment.

Preparation of an EW involves obtaining a compound of Formula (I) either as a liquid (if it is not a liquid at room temperature, it may be melted at a reasonable temperature, typically below 70° C.) or in solution (by dissolving it in an appropriate solvent) and then emulsifying the resultant liquid or solution into water containing one or more SFAs, under high shear, to produce an emulsion. Suitable solvents for use in EWs include vegetable oils, chlorinated hydrocarbons (such as chlorobenzenes), aromatic solvents (such as alkylbenzenes or alkylnaphthalenes) and other appropriate organic solvents which have a low solubility in water.

Microemulsions (ME) may be prepared by mixing water with a blend of one or more solvents with one or more SFAs, to produce spontaneously a thermodynamically stable isotropic liquid formulation. A compound of Formula (I) is present initially in either the water or the solvent/SFA blend. Suitable solvents for use in MEs include those hereinbefore described for use in in ECs or in EWs. An ME may be either an oil-in-water or a water-in-oil system (which system is present may be determined by conductivity measurements) and may be suitable for mixing water-soluble and oil-soluble pesticides in the same formulation. An ME is suitable for dilution into water, either remaining as a microemulsion or forming a conventional oil-in-water emulsion.

Suspension concentrates (SC) may comprise aqueous or non-aqueous suspensions of finely divided insoluble solid particles of a compound of Formula (I). SCs may be prepared by ball or bead milling the solid compound of Formula (I) in a suitable medium, optionally with one or more dispersing agents, to produce a fine particle suspension of the compound. One or more wetting agents may be included in the composition and a suspending agent may be included to reduce the rate at which the particles settle. Alternatively, a compound of Formula (I) may be dry milled and added to water, containing agents hereinbefore described, to produce the desired end product.

Aerosol formulations comprise a compound of Formula (I) and a suitable propellant (for example n-butane). A compound of Formula (I) may also be dissolved or dispersed in a suitable medium (for example water or a water miscible liquid, such as n-propanol) to provide compositions for use in non-pressurised, hand-actuated spray pumps.

Capsule suspensions (CS) may be prepared in a manner similar to the preparation of EW formulations but with an additional polymerisation stage such that an aqueous dispersion of oil droplets is obtained, in which each oil droplet is encapsulated by a polymeric shell and contains a compound of Formula (I) and, optionally, a carrier or diluent therefor. The polymeric shell may be produced by either an interfacial polycondensation reaction or by a coacervation procedure. The compositions may provide for controlled release of the compound of Formula (I) and they may be used for seed treatment. A compound of Formula (I) may also be formulated in a biodegradable polymeric matrix to provide a slow, controlled release of the compound.

The composition may include one or more additives to improve the biological performance of the composition, for example by improving wetting, retention or distribution on surfaces; resistance to rain on treated surfaces; or uptake or mobility of a compound of Formula (I). Such additives include surface active agents (SFAs), spray additives based on oils, for example certain mineral oils or natural plant oils (such as soy bean and rape seed oil), and blends of these with other bio-enhancing adjuvants (ingredients which may aid or modify the action of a compound of Formula (I).

Wetting agents, dispersing agents and emulsifying agents may be SFAs of the cationic, anionic, amphoteric or non-ionic type.

Suitable SFAs of the cationic type include quaternary ammonium compounds (for example cetyltrimethyl ammonium bromide), imidazolines and amine salts.

Suitable anionic SFAs include alkali metals salts of fatty acids, salts of aliphatic monoesters of sulphuric acid (for example sodium lauryl sulphate), salts of sulphonated aromatic compounds (for example sodium dodecylbenzenesulphonate, calcium dodecylbenzenesulphonate, butylnaphthalene sulphonate and mixtures of sodium di-isopropyl- and tri-isopropyl-naphthalene sulphonates), ether sulphates, alcohol ether sulphates (for example sodium laureth-3-sulphate), ether carboxylates (for example sodium laureth-3-carboxylate), phosphate esters (products from the reaction between one or more fatty alcohols and phosphoric acid (predominately mono-esters) or phosphorus pentoxide (predominately di-esters), for example the reaction between lauryl alcohol and tetraphosphoric acid; additionally these products may be ethoxylated), sulphosuccinamates, paraffin or olefine sulphonates, taurates and lignosulphonates.

Suitable SFAs of the amphoteric type include betaines, propionates and glycinates.

Suitable SFAs of the non-ionic type include condensation products of alkylene oxides, such as ethylene oxide, propylene oxide, butylene oxide or mixtures thereof, with fatty alcohols (such as oleyl alcohol or cetyl alcohol) or with alkylphenols (such as octylphenol, nonylphenol or octylcresol); partial esters derived from long chain fatty acids or hexitol anhydrides; condensation products of said partial esters with ethylene oxide; block polymers (comprising ethylene oxide and propylene oxide); alkanolamides; simple esters (for example fatty acid polyethylene glycol esters); amine oxides (for example lauryl dimethyl amine oxide); and lecithins.

Suitable suspending agents include hydrophilic colloids (such as polysaccharides, polyvinylpyrrolidone or sodium carboxymethylcellulose) and swelling clays (such as bentonite or attapulgite).

The composition of the present may further comprise at least one additional pesticide. For example, the compounds according to the invention can also be used in combination with other herbicides or plant growth regulators. In a preferred embodiment the additional pesticide is a herbicide and/or herbicide safener. Examples of such mixtures are (in which 'I' represents a compound of Formula I). I+acetochlor, I+acifluorfen, I+acifluorfen-sodium, I+aclonifen, I+acrolein, I+alachlor, I+alloxydim, I+ametryn, I+amicarbazone, I+amidosulfuron, I+aminopyralid, I+amitrole, I+anilofos, I+asulam, I+atrazine, I+azafenidin, I+azimsulfuron, I+BCPC, I+beflubutamid, I+benazolin, I+bencarbazone, I+benfluralin, I+benfuresate, I+bensulfuron, I+bensulfuron-methyl, I+bensulide, I+bentazone, I+benzfendizone, I+benzobicyclon, I+benzofenap, I+bicyclopyrone, I+bifenox, I+bilanafos, I+bispyribac, I+bispyribac-sodium, I+borax, I+bromacil, I+bromobutide, I+bromoxynil, I+butachlor, I+butamifos, I+butralin, I+butroxydim, I+butylate, I+cacodylic acid, I+calcium chlorate, I+cafenstrole, I+carbetamide, I+carfentrazone, I+carfentrazone-ethyl, I+chlorflurenol, I+chlorflurenol-methyl, I+chloridazon, I+chlorimuron, I+chlorimuron-ethyl, I+chloroacetic acid, I+chlorotoluron, I+chlorpropham, I+chlorsulfuron, I+chlorthal, I+chlorthal-dimethyl, I+cinidon-ethyl, I+cinmethylin, I+cinosulfuron, I+cisanilide, I+clethodim, I+clodinafop, I+clodinafop-propargyl, I+clomazone, I+clomeprop, I+clopyralid, I+cloransulam, I+cloransulam-methyl, I+cyanazine, I+cycloate, I+cyclopyrimorate, I+cyclosulfamuron, I+cycloxydim, I+cyhalofop, I+cyhalofop-butyl, I+2,4-D, I+daimuron, I+dalapon, I+dazomet, I+2,4-DB, I+I+desmedipham, I+dicamba, I+dichlobenil, I+dichlorprop, I+dichlorprop-P, I+diclofop, I+diclofop-methyl, I+diclosulam, I+difenzoquat, I+difenzoquat metilsulfate, I+diflufenican, I+diflufenzopyr, I+dimefuron, I+dimepiperate, I+dimethachlor, I+dimethametryn, I+dimethenamid, I+dimethenamid-P, I+dimethipin, I+dimethylarsinic acid, I+dinitramine, I+dinoterb, I+diphenamid, I+dipropetryn, I+diquat, I+diquat dibromide, I+dithiopyr, I+diuron, I+endothal, I+EPTC, I+esprocarb, I+ethalfluralin, I+ethametsulfuron, I+ethametsulfuron-methyl, I+ethephon, I+ethofumesate, I+ethoxyfen, I+ethoxysulfuron, I+etobenzanid, I+fenoxaprop-P, I+fenoxasulfone, I+fenoxaprop-P-ethyl, I+fenquinotrione, I+fentrazamide, I+ferrous sulfate, I+flamprop-M, I+flazasulfuron, I+florasulam, I+fluazifop, I+fluazifop-butyl, I+fluazifop-P, I+fluazifop-P-butyl, I+fluazolate, I+flucarbazone, I+flucarbazone-sodium, I+flucetosulfuron, I+fluchloralin, I+flufenacet, I+flufenpyr, I+flufenpyr-ethyl, I+flumetralin, I+flumetsulam, I+flumiclorac, I+flumiclorac-pentyl, I+flumioxazin, I+flumipropin, I+fluometuron, I+fluoroglycofen, I+fluoroglycofen-ethyl, I+fluoxaprop, I+flupoxam, I+flupropacil, I+flupropanate, I+flupyrsulfuron, I+flupyrsulfuron-methyl-sodium, I+flurenol, I+fluridone, I+flurochloridone, I+fluroxypyr, I+flurtamone, I+fluthiacet, I+fluthiacet-methyl, I+fomesafen, I+foramsulfuron, I+fosamine, I+glufosinate, I+glufosinate-ammonium, I+glyphosate, I+halauxifen, I+halosulfuron, I+halosulfuron-methyl, I+haloxyfop, I+haloxyfop-P, I+hexazinone, I+imazamethabenz, I+imazamethabenz-methyl, I+imazamox, I+imazapic, I+imazapyr, I+imazaquin, I+imazethapyr, I+imazosulfuron, I+indanofan, I+indaziflam, I+iodomethane, I+iofensulfuron, I+iodosulfuron, I+iodosulfuron-methyl-sodium, I+ioxynil, I+Ipfencarbazone, I+isoproturon, I+isouron, I+isoxaben, I+isoxachlortole, I+isoxaflutole, I+isoxapyrifop, I+karbutilate, I+lactofen, I+lenacil, I+linuron, I+mecoprop, I+mecoprop-P, I+mefenacet, I+mefluidide, I+mesosulfuron, I+mesosulfuron-methyl, I+mesotrione, I+metam, I+metamifop, I+metamitron, I+metazachlor, I+metazosulfuron, I+methabenzthiazuron, I+methazole, I+methiozolin, I+methylarsonic acid, I+methyldymron, I+methyl isothiocyanate, I+metolachlor, I+S-metolachlor, I+metosulam, I+metoxuron, I+metribuzin, I+metsulfuron, I+metsulfuron-methyl, I+molinate, I+monolinuron, I+naproanilide, I+napropamide, I+naptalam, I+neburon, I+nicosulfuron, I+n-methyl glyphosate, I+nonanoic acid, I+norflurazon, I+oleic acid (fatty acids), I+orbencarb, I+orthosulfamuron, I+oryzalin, I+oxadiargyl, I+oxadiazon, I+oxasulfuron, I+oxaziclomefone, I+oxyfluorfen, I+paraquat, I+paraquat dichloride, I+pebulate, I+pendimethalin, I+penoxsulam, I+pentachlorophenol, I+pentanochlor, I+pentoxazone, I+pethoxamid, I+phenmedipham, I+picloram, I+picolinafen, I+pinoxaden, I+piperophos, I+pretilachlor, I+primisulfuron, I+primisulfuron-methyl, I+prodiamine, I+profoxydim, I+prohexadione-calcium, I+prometon, I+prometryn, I+propachlor, I+propanil, I+propaquizafop, I+propazine, I+propham, I+propisochlor, I+propoxycarbazone, I+propoxycarbazone-sodium, I+propyrisulfuron, I+propyzamide, I+prosulfocarb, I+prosulfuron, I+pyraclonil, I+pyraflufen, I+pyraflufen-ethyl, I+pyrasulfotole, I+pyrazolynate, I+pyrazosulfuron, I+pyrazosulfuron-ethyl, I+pyrazoxyfen, I+pyribenzoxim, I+pyributicarb, I+pyridafol, I+pyridate, I+pyriftalid, I+pyriminobac, I+pyriminobac-methyl, I+pyrimisulfan, I+pyrithiobac, I+pyrithiobac-sodium, I+pyroxasulfone, I+pyroxsulam, I+quinclorac, I+quinmerac, I+quinoclamine, I+quizalofop, I+quizalofop-P, I+rimsulfuron, I+saflufenacil, I+sethoxydim, I+siduron, I+simazine, I+simetryn, I+sodium chlorate, I+sulcotrione, I+sulfentrazone, I+sulfometuron, I+sulfometuron-methyl, I+sulfosate, I+sulfosulfuron, I+sulfuric acid, I+tebuthiuron, I+tefuryltrione, I+tembotrione, I+tepraloxydim, I+terbacil, I+terbumeton, I+terbuthylazine, I+terbutryn, I+thenylchlor, I+thiazopyr, I+thifensulfuron, I+thiencarbazone, I+thifensulfuron-methyl, I+thiobencarb, I+tiafenacil, I+tolpyralate, I+topramezone, I+tralkoxydim, I+triafamone, I+tri-allate, I+triasulfuron, I+triaziflam, I+tribenuron, I+tribenuron-methyl, I+triclopyr, I+trietazine, I+trifloxysulfuron, I+trifloxysulfuron-sodium, I+trifludimoxazin, I+trifluralin, I+triflusulfuron, I+triflusulfuron-methyl, I+trihydroxytriazine, I+trinexapac-ethyl, I+tritosulfuron, I+[3-[2-chloro-4-fluoro-5-(1-methyl-6-trifluoromethyl-2,4-dioxo-1,2,3,4-tetrahydropyrimidin-3-yl)phenoxy]-2-pyridyloxy]acetic acid ethyl ester (CAS RN 353292-31-6). The compounds of the present invention may also be combined with herbicidal compounds disclosed in WO06/024820 and/or WO07/096576.

The mixing partners of the compound of Formula I may also be in the form of esters or salts, as mentioned e.g. in The Pesticide Manual, Sixteenth Edition, British Crop Protection Council, 2012.

The compound of Formula I can also be used in mixtures with other agrochemicals such as fungicides, nematicides or insecticides, examples of which are given in The Pesticide Manual.

The mixing ratio of the compound of Formula I to the mixing partner is preferably from 1:100 to 1000:1.

The mixtures can advantageously be used in the above-mentioned formulations (in which case "active ingredient" relates to the respective mixture of compound of Formula I with the mixing partner).

The compounds of Formula I according to the invention can also be used in combination with one or more safeners. Likewise, mixtures of a compound of Formula I according to the invention with one or more further herbicides can also be used in combination with one or more safeners. The safeners can be AD 67 (MON 4660), benoxacor, cloquintocet-mexyl, cyprosulfamide (CAS RN 221667-31-8), dichlormid, fenchlorazole-ethyl, fenclorim, fluxofenim, furilazole and the corresponding R isomer, isoxadifen-ethyl, mefenpyr-diethyl, oxabetrinil, N-isopropyl-4-(2-methoxybenzoylsulfamoyl)-benzamide (CAS RN 221668-34-4). Other possibilities include safener compounds disclosed in, for example, EP0365484 e.g. N-(2-methoxybenzoyl)-4-[(methylaminocarbonyl)amino]benzenesulfonamide. Particularly preferred are mixtures of a compound of Formula I with cyprosulfamide, isoxadifen-ethyl, cloquintocet-mexyl and/or N-(2-methoxybenzoyl)-4-[(methyl-aminocarbonyl)amino]benzenesulfonamide.

The safeners of the compound of Formula I may also be in the form of esters or salts, as mentioned e.g. in The Pesticide Manual, $16^{th}$ Edition (BCPC), 2012. The reference to cloquintocet-mexyl also applies to a lithium, sodium, potassium, calcium, magnesium, aluminium, iron, ammonium, quaternary ammonium, sulfonium or phosphonium salt thereof as disclosed in WO 02/34048, and the reference to fenchlorazole-ethyl also applies to fenchlorazole, etc.

Preferably the mixing ratio of compound of Formula I to safener is from 100:1 to 1:10, especially from 20:1 to 1:1.

The mixtures can advantageously be used in the above-mentioned formulations (in which case "active ingredient" relates to the respective mixture of compound of Formula I with the safener).

The present invention still further provides a method of controlling weeds at a locus said method comprising application to the locus a weed controlling amount of a composition comprising a compound of Formula (I). Moreover, the present invention further provides a method of selectively controlling weeds at a locus comprising crop plants and weeds, wherein the method comprises application to the locus a weed controlling amount of a composition according to the present invention. 'Controlling' means killing, reducing or retarding growth or preventing or reducing germination. Generally the plants to be controlled are unwanted plants (weeds). 'Locus' means the area in which the plants are growing or will grow. Some crop plants may be inherently tolerant to herbicidal effects of compounds of Formula (I). However, in some instances tolerance may need to be engineered into the crop plant, for example by way of genetic engineering. Thus, it is possible that the crop plant is rendered tolerant to HPPD-inhibitors via genetic engineering. Methods of rending crop plants tolerant to HPPD-inhibitors are known, for example from WO0246387. Thus in an even more preferred embodiment the crop plant is transgenic in respect of a polynucleotide comprising a DNA sequence which encodes an HPPD-inhibitor resistant HPPD enzyme derived from a bacterium, more particularly from *Pseudomonas fluorescens* or *Shewanella colwelliana*, or from a plant, more particularly, derived from a monocot plant or, yet more particularly, from a barley, maize, wheat, rice, *Brachiaria, Cenchrus, Lolium, Festuca, Setaria, Eleusine, Sorghum* or *Avena* species. Several HPPD-tolerant soybean transgenic "events" are known, and include for example SYHT04R (WO2012/082542), SYHTOH2 (WO2012/082548) and FG72. Crop plants in which the composition according to the invention can be used thus include crops such as cereals, for example barley and wheat, cotton, oilseed rape, sunflower, maize, rice, soybeans, sugar beet, sugar cane and turf. The compounds of the present invention have particular utility in maize, due to the improved selectivity observed.

Crop plants can also include trees, such as fruit trees, palm trees, coconut trees or other nuts. Also included are vines such as grapes, fruit bushes, fruit plants and vegetables.

The rates of application of compounds of Formula I may vary within wide limits and depend on the nature of the soil, the method of application (pre- or post-emergence; seed dressing; application to the seed furrow; no tillage application etc.), the crop plant, the weed(s) to be controlled, the prevailing climatic conditions, and other factors governed by the method of application, the time of application and the target crop. The compounds of Formula I according to the invention are generally applied at a rate of from 10 to 2000 g/ha, especially from 10 to 1000 g/ha, more especially from 10 to 200 g/ha.

The application is generally made by spraying the composition, typically by tractor mounted sprayer for large areas, but other methods such as dusting (for powders), drip or drench can also be used.

Crop plants are to be understood as also including those crop plants which have been rendered tolerant to herbicides or classes of herbicides (e.g. ALS-, GS-, EPSPS-, PPO-, ACCase- and HPPD-inhibitors) by conventional methods of breeding or by genetic engineering. An example of a crop that has been rendered tolerant to imidazolinones, e.g. imazamox, by conventional methods of breeding is Clearfield® summer rape (canola). Examples of crops that have been rendered tolerant to herbicides by genetic engineering methods include e.g. glyphosate- and glufosinate-resistant maize varieties commercially available under the trade names RoundupReady® and LibertyLink®.

Crop plants are also to be understood as being those which have been rendered resistant to harmful insects by genetic engineering methods, for example Bt maize (resistant to European corn borer), Bt cotton (resistant to cotton boll weevil) and also Bt potatoes (resistant to Colorado beetle). Examples of Bt maize are the Bt 176 maize hybrids of NK® (Syngenta Seeds). The Bt toxin is a protein that is formed naturally by *Bacillus thuringiensis* soil bacteria. Examples of toxins, or transgenic plants able to synthesise such toxins, are described in EP-A-451 878, EP-A-374 753, WO 93/07278, WO 95/34656, WO 03/052073 and EP-A-427 529. Examples of transgenic plants comprising one or more genes that code for an insecticidal resistance and express one or more toxins are KnockOut® (maize), Yield Gard® (maize), NuCOTIN33B® (cotton), Bollgard® (cotton), NewLeaf® (potatoes), NatureGard® and Protexcta®. Plant crops or seed material thereof can be both resistant to herbicides and, at the same time, resistant to insect feeding ("stacked" transgenic events). For example, seed can have the ability to express an insecticidal Cry3 protein while at the same time being tolerant to glyphosate.

Crop plants are also to be understood to include those which are obtained by conventional methods of breeding or genetic engineering and contain so-called output traits (e.g. improved storage stability, higher nutritional value and improved flavour).

Other useful plants include turf grass for example in golf-courses, lawns, parks and roadsides, or grown commercially for sod, and ornamental plants such as flowers or bushes.

The compositions can be used to control unwanted plants (collectively, 'weeds'). The weeds to be controlled may be both monocotyledonous species, for example *Agrostis, Alopecurus, Avena, Brachiaria, Bromus, Cenchrus, Cyperus, Digitaria, Echinochloa, Eleusine, Lolium, Monochoria, Rottboellia, Sagittaria, Scirpus, Setaria* and *Sorghum*, and dicotyledonous species, for example *Abutilon, Amaranthus, Ambrosia, Chenopodium, Chrysanthemum, Conyza, Galium, Ipomoea, Nasturtium, Sida, Sinapis, Solanum, Stellaria, Veronica,* Viola and *Xanthium*. Weeds can also include plants which may be considered crop plants but which are growing outside a crop area ('escapes'), or which grow from seed left over from a previous planting of a different crop ('volunteers'). Such volunteers or escapes may be tolerant to certain other herbicides.

The present invention further provides a compound of Formula (IV):

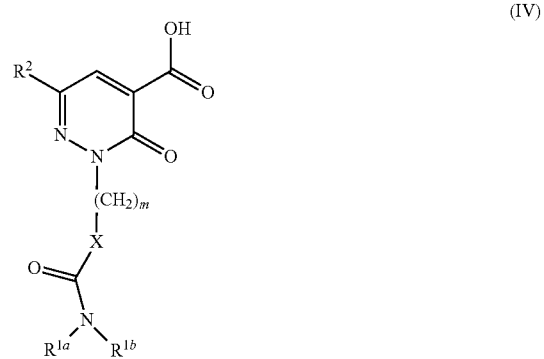

(IV)

wherein $R^{1a}$ is selected from the group consisting of hydrogen, $C_1$-$C_6$alkyl and $C_1$-$C_6$haloalkyl;

$R^{1b}$ is selected from the group consisting of hydrogen, $C_1$-$C_6$alkyl, $C_1$-$C_3$alkoxy- and $C_1$-$C_6$haloalkyl; or $R^{1a}$ and $R^{1b}$ together are —CH$_2$CH$_2$CH$_2$CH$_2$—, —CH$_2$CH$_2$CH$_2$CH$_2$CH$_2$— or —CH$_2$CH$_2$OCH$_2$CH$_2$—; and X is selected from the group consisting of O, —CF$_2$—, —C(CH$_3$)— and —CH$_2$—;

m is 0, 1 or 2 wherein if X is O then m is 1 or 2; and $R^2$ is selected from the group consisting of hydrogen, $C_1$-$C_6$alkyl and $C_3$-$C_6$cycloalkyl.

The compounds of the present invention can be prepared according to the following schemes. $R^a$, $R^b$, $R^c$, $R^d$, $A^1$, $R^2$, $R^{1a}$, $R^{1b}$, m and X are as defined previously.

Scheme 1

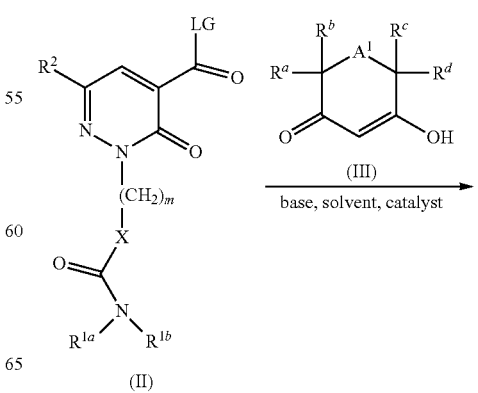

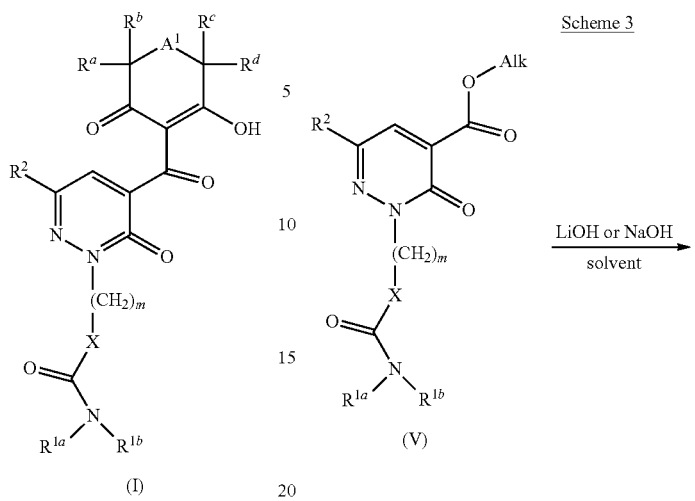

(I)

In one suitable method, compounds of formula (I) can be prepared from compounds of formula (II) and compounds of formula (III), where LG is defined as a leaving group. Examples of suitable leaving groups are chloride and N-linked imdazolyl. An example of a suitable base is triethylamine and an example of a suitable catalyst is acetone cyanohydrin. An example of a suitable solvent is dichloromethane.

Scheme 2

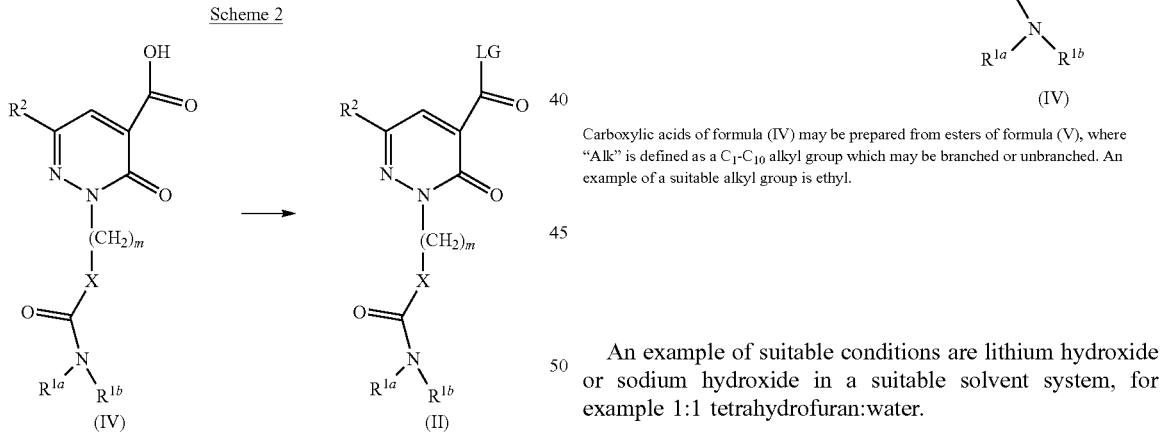

Compounds of formula (II) can be prepared from carboxylic acids of formula (IV). The compounds of formula (II) may be isolated, or compounds of formula (I) may be prepared directly from compounds of formula (IV) without isolation of compounds of formula (II).

For example, where LG=chloro, carboxylic acids of formula (II) may be treated with a chlorination reagent such as oxalyl chloride in a suitable solvent such as dichloromethane. In another example where LG=N-linked imidazolyl, carboxylic acids of formula (II) may be treated with carbonyldimiidazole in a suitable solvent such as N,N-dimethylformamide or dichloromethane.

Scheme 3

(V) → LiOH or NaOH / solvent →

(IV)

Carboxylic acids of formula (IV) may be prepared from esters of formula (V), where "Alk" is defined as a $C_1$-$C_{10}$ alkyl group which may be branched or unbranched. An example of a suitable alkyl group is ethyl.

An example of suitable conditions are lithium hydroxide or sodium hydroxide in a suitable solvent system, for example 1:1 tetrahydrofuran:water.

Scheme 4

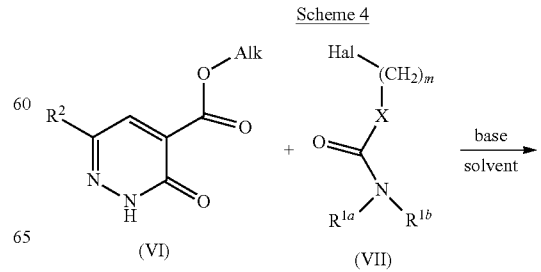

-continued

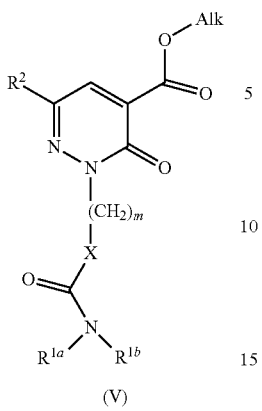

(V)

Compounds of formula (V) may be prepared from the combination of compounds of formula (VI) and alkylating agents of formula (VII), where "Hal" is defined as chloro, bromo or iodo.

Suitable conditions to perform this alkylation reaction are: a base, for example sodium hydride, potassium carbonate or caesium carbonate in a suitable solvent, for example N,N-dimethylformamide.

Scheme 5

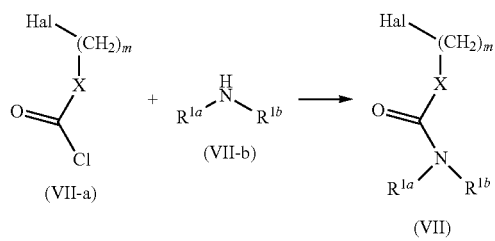

Compounds of formula (VII) may be commercially available, or may be synthesised from known methods. As a non-limiting example, compounds of formula (VII) may be prepared from acyl chlorides of formula (VII-a) and amines of formula (VII-b).

Scheme 6

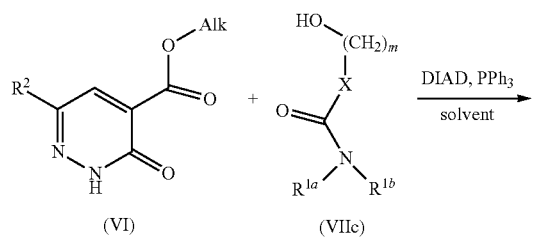

-continued

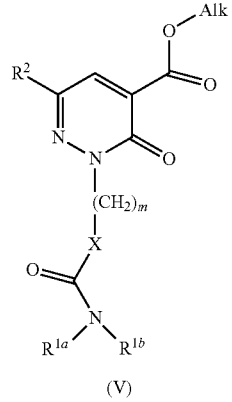

(V)

Alternatively, compounds of formula (V) may be prepared from alcohols of formula (VII-c) by Mitsunobu reaction.

An example of suitable conditions for this Mitsunobu reaction are diisopropyldiazodicarboxylate (DIAD) and triphenylphosphine. An example of a suitable solvent for this reaction is tetrahydrofuran.

Scheme 7

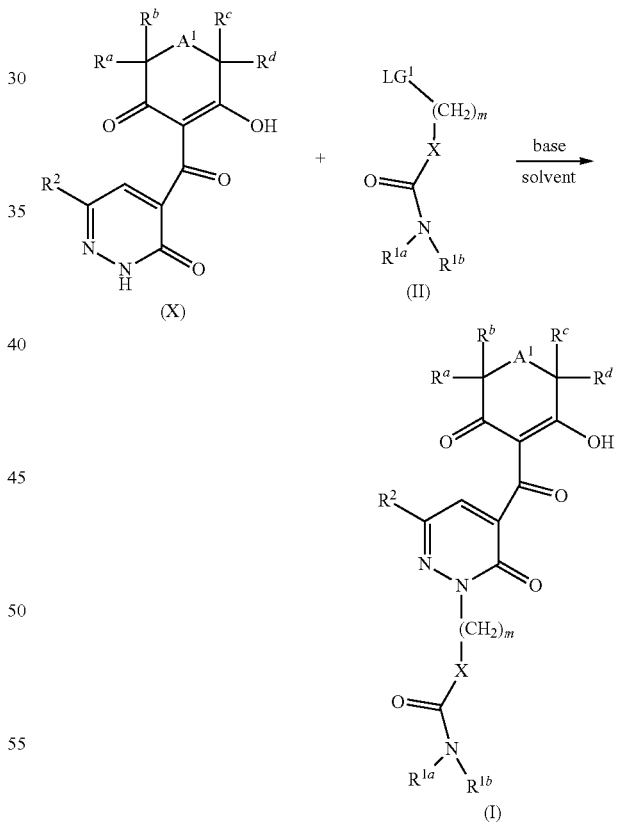

Compounds of formula (II) alternatively may be prepared via the combination of compounds of formula X with alkylating agents of formula VII, where "LG$^1$" is a leaving group, for example chloro, bromo, iodo, tosylate, mesylate or triflate.

Examples of suitable bases are: caesium carbonate, potassium carbonate, sodium hydride and lithium hexamethyldisilazide. Examples of suitable solvents are N,N-dimethylformamide or tetrahydrofuran. At least 2 molar equivalents of the base will be necessary to perform this transformation.

Scheme 8

(XI) —HCl in methanol→ (XI)

Compounds of formula (XI) may be prepared from carboxylic acids of formula (XII) and diketones of formula (III) by preactivation with carbonyldiimidazole, followed by the addition of diones of formula (III) and a catalyst. An example of suitable catalyst is acetone cyanohydrin. Examples of suitable solvents for this sequence are 1,4-dioxane and dichloromethane.

(X)

Compounds of formula (X) can be prepared from compounds of formula (XI) by treatment with HCl in methanol.

Scheme 10

(XIII) —LiOH or NaOH / solvent→ (XII)

Scheme 9

(XII) —1. carbonyldiimidazole 2. (III) 3. acetone cyanohydrin→

Carboxylic acids of formula (XII) may be prepared from esters of formula (XIII), where "Alk" is a C1-C10 alkyl chain that may be branched or unbranched. This can be achieved by treatment with a hydroxide base such as lithium hydroxide or sodium hydroxide and a suitable solvent system. An example of a suitable solvent system is a 1:1 mixture of tetrahydrofuran:water.

Scheme 11

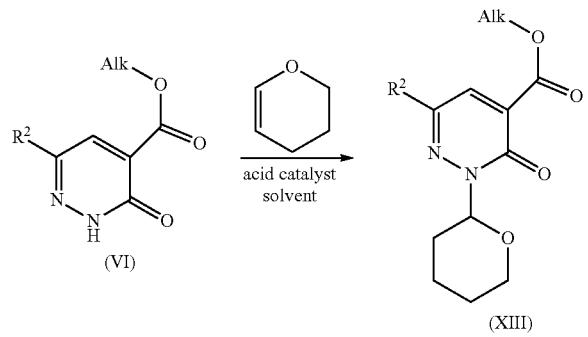

Compounds of formula (XIII) may be prepared from compounds of formula (VI).

Compounds of formula (VI) are treated with dihydropyran and an acid catalyst in a suitable solvent. An example of a suitable acid catalyst is para-toluene sulfonic acid. An example of a suitable solvent is tetrahydrofuran.

Scheme 12

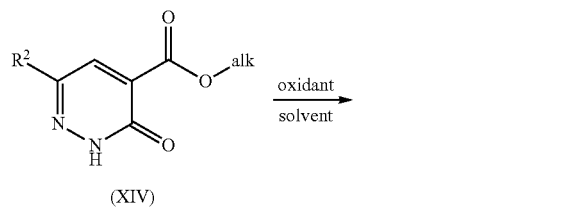

Pyridazinones of formula (VI) may be prepared by the oxidation of dihydropyridazinones of formula (XIV) with a suitable oxidant in a suitable solvent. Examples of suitable oxidiants and solvents are bromine in a solution of acetic acid or dichloromethane, or iodobenzene diacetate in a solution of isopropanol.

Scheme 13

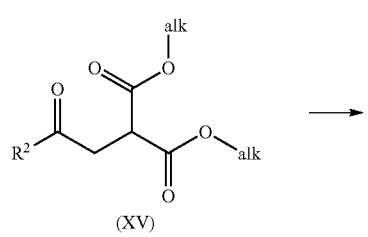

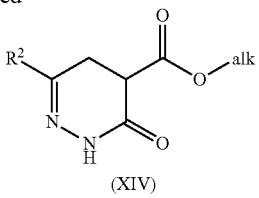

Dihydropyridazinones of formula (XIV) may br prepared through the treatment of compounds of formula (XV) with hydrazine hydrate in a suitable solvent such as ethanol under reflux conditions.

Scheme 14

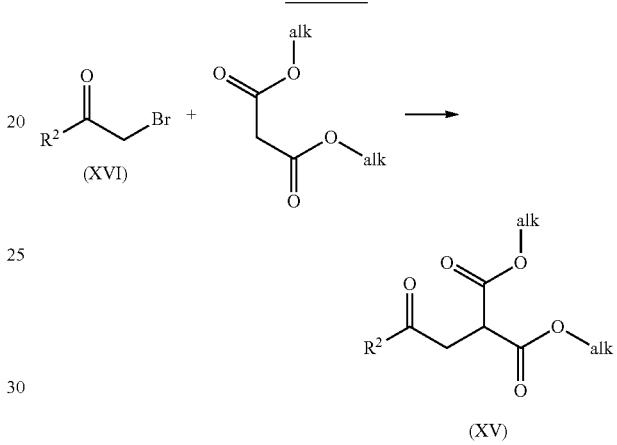

Compounds of formula (XV) may be prepared via the alkylation of a commercially available dialkyl malonate (for example diethyl malonate) with a bromo-ketone of formula (XVI) in the presence of a suitable base, for example potassium carbonate, in a suitable solvent, for example acetone.

Scheme 15

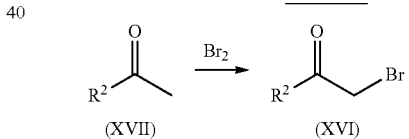

Compounds of formula (8) may be commercially available, or alternatively they may be prepared via the bromination of a commercially available methyl ketone of formula (9) by treatment with bromine in a suitable solvent such as methanol or a mixture of water and glacial acetic acid (~5:1).

The following non-limiting examples provide specific synthesis methods for representative compounds of the present invention, as referred to in Table 1 below.

PREPARATIVE EXAMPLE 1 (COMPOUND 1.002)

Step 1: Preparation of 1-Bromopropan-2-one

Acetone (150 g, 2.58 mol), water (480 mL) and glacial acetic acid (90 mL) were stirred in a two-necked round bottom flask and heated to reflux (75° C.). Bromine (73.2 mL, 2.84 mol) was added portion wise to the solution. The reaction mixture continued to be heated at 75° C. until it turned colourless. It was then cooled to 0° C. (ice-bath) and water added (100 mL) followed by sufficient Na$_2$CO$_3$ until it was no longer acidic. The reaction mixture was transferred to a separating funnel and the bottom organic layer separated, dried over Na₂SO₄ and filtered to afford 1-bromopropan-2-one.

¹H NMR (CDCl₃, 400 MHz) δ=3.23 (s, 2H), 1.67-1.72 (m, 3H).

Step 2. Preparation of Diethyl 2-acetonylpropanedioate

1-Bromopropan-2-one (90 g, 0.66 mol) was dissolved in acetone (740 mL) and under a nitrogen atmosphere. Diethylmalonate (126 mL, 0.79 mol), K₂CO₃ (136 g, 0.99 mol) and KI (3.27 g, 19.7 mmol) were added to the stirred solution. The reaction mixture was heated at reflux for 16 hours. The reaction mixture was filtered and the filtrate concentrated in vacuo. The crude material was dissolved in EtOAc and washed with water followed by brine. The organic layer was dried over Na₂SO₄, filtered and concentrated in vacuo to afford a liquid. This crude product was purified by column chromatography eluting with 0-5% MeOH in CH₂Cl₂ to afford diethyl 2-acetonylpropanedioate as a pale yellow oil.

¹H NMR (CDCl₃, 400 MHz) δ=4.21-4.04 (m, 4H), 3.78 (t, 1H), 2.99 (d, 2H), 2.20-2.06 (m, 3H), 1.27-1.13 (m, 6H).

Step 3. Preparation of Ethyl 3-methyl-6-oxo-4,5-dihydro-1H-pyridazine-5-carboxylate Diethyl 2-acetonylpropanedioate (80 g, 370 mmol) was dissolved in absolute ethanol (175 mL) and cooled to 0° C. To the stirred solution was added hydrazine hydrate (20.4 mL, 407 mmol) dropwise. The mixture was allowed to warm to room temperature and stirred for 16 hours. The reaction mixture was concentrated in vacuo and the resultant crude ethyl 3-methyl-6-oxo-4,5-dihydro-1H-pyridazine-5-carboxylate was used directly in the next step without further purification.

Step 4. Preparation of Ethyl 3-methyl-6-oxo-1H-pyridazine-5-carboxylate

A solution of bromine (17 mL, 662 mmol) in acetic acid (140 mL) was added portion wise to a stirred solution of ethyl 3-methyl-6-oxo-4,5-dihydro-1H-pyridazine-5-carboxylate (61 g crude, 331 mmol) in acetic acid (1250 mL). The reaction mixture was stirred at room temperature for 1 hour then concentrated in vacuo. The crude material was dissolved in EtOAc and this solution washed with water followed by brine, dried over Na₂SO₄, filtered and concentrated in vacuo. The crude material was purified by column chromatography eluting with 0-5% MeOH in CH₂Cl₂ to afford ethyl 3-methyl-6-oxo-1H-pyridazine-5-carboxylate as an off-white solid.

¹H NMR (CDCl₃, 400 MHz) δ=7.71 (s, 1H), 4.40 (q, 2H), 2.39 (s, 3H), 1.39 (t, 3H).

Step 5. Preparation of Ethyl 6-methyl-3-oxo-2-tetrahydropyran-2-yl-pyridazine-4-carboxylate To a flask was added: ethyl 3-hydroxy-6-methyl-pyridazine-4-carboxylate (5 g, 27.445 mmol), dichloromethane (50 mL) and toluene-4-sulfonic acid (0.955 g, 5.4891 mmol). The mixture was cooled to 0° C. and 3,4-dihydro-2H-pyran (4.6173 g, 5.01 mL, 54.9 mmol) in DCM (5 ml) was added via dropping funnel over 30 min. Stirring was continued for 30 min. The mixture was warmed to room temperature and concentrated. The residue was partitioned between ether and water. The organic layer was separated, washed with water, then brine, dried (MgSO₄) and concentrated to give ethyl 6-methyl-3-oxo-2-tetrahydropyran-2-yl-pyridazine-4-carboxylate. The compound was taken on crude with a contaminant of dihydropyran without further purification.

Step 6. Preparation of 6-Methyl-3-oxo-2-tetrahydropyran-2-yl-pyridazine-4-carboxylic Acid To a flask was added: ethyl 6-methyl-3-oxo-2-tetrahydropyran-2-yl-pyridazine-4-carboxylate (7.4 g, 28 mmol), THF (150 mL) and sodium hydroxide aq. solution (42 mL, 83 mmol, 2 mol/L) was stirred for 20 min. The mixture was partially concentrated to remove THF, then diluted with EtOAc (40 ml) and water (~20 ml). The aqueous layer was separated, and acidified by dropwise addition of excess HCl (conc.). The resulting mixture was extracted to DCM and concentrated to give 6-methyl-3-oxo-2-tetrahydropyran-2-yl-pyridazine-4-carboxylic acid as a white crystalline solid.

¹H NMR (400 MHz, Chloroform) δ=8.09 (s, 1H), 6.08 (dd, J=2.2, 10.6 Hz, 1H), 4.21-4.14 (m, 1H), 3.77 (dt, J=2.8, 11.6 Hz, 1H), 2.51 (s, 3H), 2.33-2.20 (m, 1H), 2.14-2.06 (m, 1H), 1.79-1.69 (m, 3H), 1.65-1.59 (m, 1H)

Step 7. Preparation of 2-(6-methyl-3-oxo-2-tetrahydropyran-2-yl-pyridazine-4-carbonyl)cyclohexane-1,3-dione To a flask equipped with a nitrogen bubbler was added: 6-methyl-3-oxo-2-tetrahydropyran-2-yl-pyridazine-4-carboxylic acid (13.0 g, 54.6 mmol) and 1,4-dioxane (130 mL). The mixture was warmed to 90° C. (remained cloudy) and CDI (10.95 g, 65.5 mmol) was added in 4 portions over 30 min, maintaining a gradual rate of effervescence. Heating was continued for 1 h, after which time effervescence had stopped. Further CDI (5.47 g, 32.7 mmol) was added and stirring continued for 1 h. The mixture was concentrated and the residue was redissolved in CH₂Cl₂ (200 mL). The solution was cooled in an ice bath then charged with cyclohexane-1,3-dione (6.12 g, 54.6 mmol) in a single portion, followed by triethylamine (22.1 g, 30.3 mL, 218.3 mmol) in a single portion. The mixture was stirred for 5 min then the ice bath removed and the mixture stirred for a further 25 min. Further cyclohexane-1,3-dione (1.2 g, 0.2 eq.) was added and stirring was continued for 1 h. The mixture was then stored in the freezer overnight. Acetone cyanohydrin (0.697 g, 0.747 mL, 8.18 mmol, 100 mass %) was added and the mixture warmed to 40° C. for 1 h. Further triethylamine (22.09 g, 30.3 mL, 218 mmol) and acetone cyanohydrin (0.697 g, 0.747 mL, 8.18 mmol) were added. The mixture was stirred at 40° C. for a further 1 h. The mixture was cooled and concentrated under reduced pressure. The residue was dissolved in DCM and purified by flash chromatography (silica, 330 g; 20:8:4:4:1 toluene:1,4-dioxane:triethylamine:ethanol:water). The desired fractions were combined and concentrated. The residue was partitioned between dilute HCl (2 M, 200 ml) and EtOAc (200 ml). The organic layer was separated and extracted with sat. NaHCO₃ (2×100 ml). The combined extracts were cooled in an ice bath and acidified with excess conc. HCl. The rate of addition was controlled to maintain the temperature below 20° C.). The aqueous layer was then extracted to toluene (100 ml) and the organics dried (MgSO₄) and concentrated to give 2-(6-methyl-3-oxo-2-tetrahydropyran-2-yl-pyridazine-4-carbonyl)cyclohexane-1,3-dione as a brown foaming solid.

¹H NMR (400 MHz, Chloroform) δ=6.99 (s, 1H), 6.11-5.94 (m, 1H), 4.14 (td, J=2.0, 11.5 Hz, 1H), 3.79-3.65 (m, 1H), 2.78-2.69 (m, 2H), 2.58-2.48 (m, 1H), 2.48-2.40 (m, 1H), 2.38 (s, 3H), 2.28-2.15 (m, 1H), 2.14-1.94 (m, 3H), 1.78-1.65 (m, 3H), 1.59-1.51 (m, 1H).

Step 8. Preparation of 2-(3-methyl-6-oxo-1H-pyridazine-5-carbonyl)cyclohexane-1,3-dione To a flask was added 2-(6-methyl-3-oxo-2-tetrahydropyran-2-yl-pyridazine-4-carbonyl)cyclohexane-1,3-dione (0.2 g, 0.6018 mmol), methanol (2 mL) and concentrated hydrochloric acid (0.119 g, 0.2 mL, 3.26 mmol). The mixture was heated to 70° C. for 35 min. The mixture was concentrated and the residue partitioned between DCM and NaHCO₃ solution. The aqueous layer was separated and acidified with excess conc. HCl, then extracted with DCM (×2). The combined extracts were dried (MgSO₄) and concentrated to give 2-(3-methyl-6-oxo-1H-pyridazine-5-carbonyl)cyclohexane-1,3-dione as a white solid.

¹H NMR (400 MHz, Chloroform) δ=10.95-10.58 (m, 1H), 7.09 (s, 1H), 2.75 (t, J=6.4 Hz, 2H), 2.57-2.45 (m, 2H), 2.35 (s, 3H), 2.15-2.01 (m, 2H)

Step 9. Preparation of Sodium 2-[2-[3-(dimethylamino)-3-oxo-propyl]-6-methyl-3-oxo-pyridazine-4-carbonyl]-3-oxo-cyclohexen-1-olate To a stirred mixture of 2-(3-methyl-6-oxo-1H-pyridazine-5-carbonyl)cyclohexane-1,3-dione (5.00 g, 20.1 mmol), cesium carbonate (32.8 g, 101 mmol) and sodium iodide (6.04 g, 40.3 mmol) in anhydrous dimethylformamide (100 mL) at room temperature and under nitrogen was added 3-chloro-N,N-dimethyl-propanamide (3.55 g, 26.2 mmol) in one portion. The mixture was heated at 130° C. for 2 h 45 min. The reaction mixture was cooled to room temperature, acidified with 2M HCl and extracted with DCM. The organic phase was washed with brine, dried over magnesium sulfate, filtered and concentrated in vacuo (removing DMF on the Hi-Vac) to afford a brown solid. The solid was dissolved in DCM and extracted into sat. aq. NaHCO₃ solution (×3). The combined aqueous extracts were acidified to pH 1 (conc. HCl) and then extracted into DCM (×3). The combined organics were washed with brine, dried over magnesium sulfate, filtered and concentrated in vacuo to afford a beige solid. This was adsorbed onto silica and purified by automated column chromatography (120 g silica cartridge, 0 to 10% methanol in 20:8:4:4:1 toluene:dioxane:triethylamine:ethanol:water) to give a yellow gum. To this gum was 5 added 2M HCl (50 mL) and DCM (50 mL) and the mixture stirred for 5 minutes. The phases were separated through a phase separation cartridge, washing with DCM. The filtrate was concentrated in vacuo to afford a yellow solid. The solid was ground to a powder in a pestle and mortar and stirred at room temperature as a suspension in diethyl ether (30 mL) for 3 hours. The solid was collected by filtration, washing the residue with further diethyl ether to give 3-[5-(2,6-dioxocyclohexanecarbonyl)-3-methyl-6-oxopyridazin-1-yl]-N,N-dimethyl-propanamide an off white powder.

¹H NMR (400 MHz, Chloroform) δ 16.18 (1H, br. s), 7.00 (1H, s), 4.41 (2H, t), 2.98 (3H, s), 2.93 (3H, s), 2.79 (2H, t), 2.72 (2H, t), 2.45 (2H, t), 2.32 (3H, s), 2.05 (2H, quintet).

Step 10. Preparation of Compound 1.002

3-[5-(2,6-dioxocyclohexanecarbonyl)-3-methyl-6-oxopyridazin-1-yl]-N,N-dimethyl-propanamide (4.65 g, 13.4 mmol) was partially dissolved in MeCN (30 mL) and cooled to 0° C. in an ice-salt bath. 1M NaOH (aq.) (1.00 equiv., 13.4 mL) was added portionwise over 3 minutes. The resultant solution was stirred for 2 minutes at 0° C. then allowed to warm to room temperature and stirred for a further 30 minutes. The sample was frozen in liquid nitrogen and dried overnight on the freeze drier to give sodium 2-[2-[3-(dimethylamino)-3-oxo-propyl]-6-methyl-3-oxo-pyridazine-4-carbonyl]-3-oxo-cyclohexen-1-olate as a yellow-orange solid.

¹H NMR (400 MHz, DMSO-d₆) δ=6.92 (s, 1H), 4.14 (t, J=7.6 Hz, 2H), 2.94 (s, 3H), 2.82 (s, 3H), 2.68 (t, J=7.9 Hz, 2H), 2.35 (br t, J=6.3 Hz, 4H), 2.23 (s, 3H), 1.82 (quin, J=6.1 Hz, 2H).

PREPARATIVE EXAMPLE 2 (COMPOUND 1.003)

Step 1: Preparation of 3-bromo-N,N-dimethyl-propanamide

Morpholine (5.00 g, 57.4 mmol) and bromoacetylbromide (2.4 mL, 28.7 mmol) were taken in DCM (30 mL). The reaction mass was stirred at RT for 1.5 h before being washed with NaHCO₃ solution and brine, then dried over Na2SO4. The solvent was evaporated to give 3-bromo-N,N-dimethyl-propanamide.

¹H NMR (400 MHz, CDCl3): 3.84 (2H, s), 3.83 (2H, m), 3.69 (2H, m), 3.64-3.61 (2H, m), 3.51 (2H, m).

Step 2: Preparation of Ethyl 6-methyl-2-(2-morpholino-2-oxo-ethyl)-3-oxo-pyridazine-4-carboxylate (The starting material 3-bromo-N,N-dimethyl-propanamide was prepared as detailed in Preparative example 1, steps 1 to 4).

2-(3-methyl-6-oxo-1H-pyridazine-5-carbonyl)cyclohexane-1,3-dione (1.5 g, 8.24 mmol) and 3-bromo-N,N-dimethyl-propanamide (2.40 g, 11.5 mmol) and dry Cs₂CO₃ (4.1 g, 12.4 mmol) were taken in dry DMF. The reaction mass was heated at 60° C. for 2 h. TLC showed a polar spot was formed. The reaction mass was filtered through celite, washed with DCM, acidified with citric acid, washed with 300 mL cold water and dried over Na2SO4. The solvent was evaporated and the crude reaction mass was purified with chromatography (ethyl acetate-DCM) to give ethyl 6-methyl-2-(2-morpholino-2-oxo-ethyl)-3-oxo-pyridazine-4-carboxylate.

¹H NMR (400 MHz, CDCl3): 7.67 (1H, s), 4.95 (2H, s), 4.36 (2H, q), 3.73-3.39 (8H, m), 2.37 (3H, s), 1.36 (3H, t).

Step 3. Preparation of 6-methyl-2-(2-morpholino-2-oxo-ethyl)-3-oxo-pyridazine-4-carboxylic Acid To ethyl 6-methyl-2-(2-morpholino-2-oxo-ethyl)-3-oxopyridazine-4-carboxylate (170 mg, 0.453 mmol) was added 2.0 ml ACN and 2 ml water, then added 0.4 ml NaOH solution (1 M in water, 0.40 mmol) and stirred for 15 min at room temperature. Reaction mixture was then washed with DCM (10 ml) and aqueous layer was lyophilized to give 6-methyl-2-(2-morpholino-2-oxo-ethyl)-3-oxo-pyridazine-4-carboxylic acid.

¹H NMR (400 MHz, d6-DMSO): 13.83 (1H, brs), 7.97 (1H, s), 5.09 (2H, s), 3.63 (2H, m), 3.58 (2H, m), 3.52 (2H, m), 3.44 (2H, m), 2.36 (3H, s).

Step 4. Preparation of Compound 1.003

6-methyl-2-(2-morpholino-2-oxo-ethyl)-3-oxo-pyridazine-4-carboxylic acid (490 mg, 1.74 mmol) and carbonyl diimidazole (480 mg, 2.96 mmol) were taken in 1,4-dioxane (2 mL) and reaction mass was heated at 110° C. for 3 h. 1,3-cyclohexanedione (235 mg, 2.09 mmol) and DBU (0.26 mL, 1.74 mmol) was added to it and heated at same temperature for 60 min. Triethylamine (0.728 mL, 5.226 mmol) and acetone cyanohydrin (7 drops) were added and stirred at RT for 16 h. The reaction mass was purified by chromatography with a solvent system of 20:8:4:4:1 toluene:1,4-dioxane:triethylamine:ethanol:water. The fractions containing product were evaporated, acidified using citric acid and extracted with DCM. After evaporation of the solvent, the residue was then purified further by chromatography (acetone-DCM) to get pure compound. The compound was lyophilised with acetonitrile and water but the compound partially decomposed in acetonitrile. That material was further purified with chromatography (acetone-DCM) to give 2-[6-methyl-2-(2-morpholino-2-oxo-ethyl)-3-oxo-pyridazine-4-carbonyl]cyclohexane-1,3-dione.

$^1$H NMR (CDCl3): 16.11 (1H, s), 7.08 (1H, s), 4.90 (2H, s), 3.68-3.61 (6H, m), 3.47 (2H, m), 2.71 (2H, t), 2.45 (2H, t), 2.35 (3H, s), 2.06-2.02 (2H, m).

PREPARATIVE EXAMPLE 3 (COMPOUND 1.011)

Step 1. Preparation of 3-bromo-N,N-dimethyl-propanamide

To the solution of 3-bromopropanoyl chloride (10.0 g, 58.3 mmol) in DCM (60 mL) under nitrogen and on an ice bath was added 60 ml solution of dimethyl-amine (2.0 M in THF, 120.68 mmol) drop wise and finally stirred at room temperature for 3 h. The reaction mass was diluted with DCM (150 ml) and washed with water (30 ml). The DCM layer was then washed with aq. solution of NaHCO$_3$ (50 ml), then with brine (50 ml), dried over Na$_2$SO$_4$, filtered and concentrated to give 3-bromo-N,N-dimethyl-propanamide. The product was used crude in the next step.

$^1$H NMR (400 MHz, CDC3): 3.63 (2H, t), 3.00 (3H, s), 2.95 (3H, s), 2.89 (2H, t).

Step 2. Preparation of Ethyl 2-[3-(dimethylamino)-3-oxo-propyl]-6-methyl-3-oxo-pyridazine-4-carboxylate (The starting material 3-bromo-N,N-dimethyl-propanamide was prepared as detailed in Preparative example 1, steps 1 to 4)

To a solution of 2-(3-methyl-6-oxo-1H-pyridazine-5-carbonyl)cyclohexane-1,3-dione (2.0 g, 11.0 mmol) in DMF (40 ml) under nitrogen was added freshly dried Cs$_2$CO$_3$ (2.94 g, 12.1 mmol) and stirred at room temperature for 2 h. Then a solution of 3-bromo-N,N-dimethyl-propanamide (2.4 g, 13.2 mmol) in DMF (20 ml) was added and stirred at room temperature for 20 h. The reaction mass was diluted with DCM (100 ml) and filtered. The filtrate was washed with ice cold water (100 ml) and the aqueous layer was again extracted with DCM (50 ml×2). The Combined DCM extracts were then washed with brine (50 ml), dried over Na$_2$SO$_4$, filtered and concentrated under reduced pressure. Crude purified by silica gel column chromatography, where the desired product was eluted with 15% solution of MeOH in DCM to give ethyl 2-[3-(dimethylamino)-3-oxo-propyl]-6-methyl-3-oxo-pyridazine-4-carboxylate. 7.95 (1H, s), 4.46 (2H, t), 4.37 (2H, q), 3.00 (3H, s), 2.93 (3H, s), 2.83 (2H, t), 2.35 (3H, s), 1.37 (3H, t).

Step 3. Preparation of 2-[3-(dimethylamino)-3-oxo-propyl]-6-methyl-3-oxo-pyridazine-4-carboxylic Acid Ethyl 2-[3-(dimethylamino)-3-oxo-propyl]-6-methyl-3-oxo-pyridazine-4-carboxylate (3.0 gm, 10.66 mmol) was dissolved in pyridine (20 mL). To it lithium iodide (3.57 gm, 26.7 mmol) was added and stirred at 110° C. for 15 h. The pyridine was evaporated under reduced pressure. The crude reaction mass was partitioned between DCM and water. The water layer was separated and acidified with 10% citric acid solution in water and extracted with DCM (100 ml×3). The combined DCM extracts were dried over Na2SO4, filtered and evaporated to get the crude product, which was triturated with 50% solution of Et2O in Hexane to get pure 2-[3-(dimethylamino)-3-oxo-propyl]-6-methyl-3-oxo-pyridazine-4-carboxylic acid as a light yellow solid.

$^1$H NMR (400 MHz, d6-DMSO): 14.09 (1H, brs), 7.97 (1H, s), 4.31 (2H, t), 2.94 (3H, s), 2.81 (3H, s), 2.81 (2H, t), 2.37 (3H, s).

Step 4. Preparation of 3-[5-(4,4-dimethyl-2,6-dioxo-cyclohexanecarbonyl)-3-methyl-6-oxo-pyridazin-1-yl]-N,N-dimethyl-propanamide To a solution of 2-[3-(dimethylamino)-3-oxo-propyl]-6-methyl-3-oxo-pyridazine-4-carboxylic acid (500 mg, 1.97 mmol) in dry dichloromethane (20 ml) and DMF (0.05 ml) at 0° C. was added oxalyl chloride (0.21 mL, 2.37 mmol) dropwise and then stirred at room temperature for 60 min. The intermediate acid chloride was concentrated under nitrogen, then re-dissolved in dry DCM (20 ml), added activated molecular sieves (powdered), cooled on ice-salt bath and added Et3N (0.83 ml, 5.93 mmol) drop wise over a period of 15 min. Then a solution of 5,5-dimethyl-1,3-cyclohexanedione (0.334 g, 2.37 mmol) in dry DCM (10 ml) was added and stirred below 0° C. for 10 min. The reaction mixture was then stirred at room temperature over 60 min, before adding Et3N (0.83 ml, 5.93 mmol) followed by acetone cyanohydrin (0.1 ml, 1.58 mmol) and stirred at room temperature for 2 h. The reaction mixture was then diluted with DCM (100 ml) and washed with aqueous solution of citric acid (acidic pH=5-4 of aqueous layer). The aqueous layer was again extracted with DCM (50 ml). The combined DCM layers were then washed with brine (50 ml), dried over Na2SO4, filtered and concentrated. The crude residue was purified by column chromatography using a solvent system of 20:8:4:4:1 toluene:1,4-dioxane:triethylamine:ethanol:water. The fractions containing desired product was then concentrated under reduced pressure, dissolved in DCM (50 ml) and washed with 1N aq. citric acid solution (25 ml), then with water (25 ml) and finally with brine (25 ml). The organic layer was dried over Na2SO4, filtered and concentrated. The resulting oil was finally purified by silica-gel column chromatography using Acetone/DCM system and the desired compound was eluted with 20% acetone in DCM to give 3-[5-(4,4-dimethyl-2,6-dioxo-cyclohexanecarbonyl)-3-methyl-6-oxo-pyridazin-1-yl]-N,N-dimethyl-propanamide.

$^1$H NMR (400 MHz, CDCl3): 7.03 (1H, s), 4.41 (2H, t), 2.98 (3H, s), 2.93 (3H, s), 2.79 (2H, t), 2.60 (2H, s), 2.34 (2H, s), 2.33 (3H, s), 1.11 (6H, s).

Step 5. Preparation of Compound 1.011

To 3-[5-(4,4-dimethyl-2,6-dioxo-cyclohexanecarbonyl)-3-methyl-6-oxo-pyridazin-1-yl]-N,N-dimethyl-propanamide (170 mg, 0.453 mmol) in was added 2.0 ml ACN and 2 ml water, then 0.40 ml NaOH solution (1 M in water, 0.40 mmol) was added and stirred for 15 min at room temperature. The reaction mixture was then washed with DCM (10 ml) and the aqueous layer was lyophilized on a freeze-dryer. After lyophilisation, sodium 2-[2-[3-(dimethylamino)-3-oxo-propyl]-6-methyl-3-oxo-pyridazine-4-carbonyl]-5,5-dimethyl-3-oxo-cyclohexen-1-olate was isolated as a yellow solid.

$^1$H NMR (400 MHz, D$_2$O) δ=7.09 (1H, s), 4.39 (2H, t), 3.05 (3H, s), 2.95 (3H, s), 2.92 (2H, t), 2.36 (3H, s), 2.34 (4H, s), 1.06 (6H, s)

PREPARATIVE EXAMPLE 4 (COMPOUND 1.012)

Step 1: Preparation of 3-[5-(2,4-dioxobicyclo[3.2.1]octane-3-carbonyl)-3-methyl-6-oxo-pyridazin-1-yl]-N,N-dimethyl-propanamide (The starting material 2-[3-(dimethylamino)-3-oxo-propyl]-6-methyl-3-oxo-pyridazine-4-carboxylic acid was prepared as detailed in Preparative example 3, steps 1 to 4)

To a solution of 2-[3-(dimethylamino)-3-oxo-propyl]-6-methyl-3-oxo-pyridazine-4-carboxylic acid (500 mg, 1.97 mmol) in dry DCM (20 ml) and DMF (0.05 ml) at 0° C. was added oxalyl chloride (0.21 ml, 2.37 mmol) dropwise and then stirred at room temperature for 60 min. The intermediate acid chloride was dried under inert atmosphere under reduced pressure. It was then re-dissolved in dry DCM (20 ml), added activated molecular sieves (powdered), cooled with an ice-salt bath and added Et3N (0.83 ml, 5.93 mmol) dropwise over a period of 15 min. Then a solution of bicyclo[3.2.1]octane-2,4-dione (0.330 gm, 2.38 mmol) in dry DCM (10 ml) was added and the reaction mixture was stirred below 0° C. for 10 min, before being stirred at room temperature for 60 min. Et3N (0.83 ml, 5.93 mmol) was added followed by acetone cyanohydrin (0.1 ml, 1.58 mmol) and the reaction mixture was stirred at room temperature for 2 h. It was then diluted with DCM (100 ml) and washed with aqueous solution of citric acid (acidic pH=5-4 of aqueous layer). The aqueous layer was again extracted with DCM (50 ml). The combined DCM layers were then washed with brine (50 ml), dried over Na2SO4, filtered and concentrated under reduced pressure. The crude material was purified by column chromatography using 20:8:4:4:1 toluene:1,4-dioxane:triethylamine:ethanol:water. The fractions containing desired product were then concentrated under reduced pressure, dissolved in DCM (50 ml) and washed with 1N aq. citric acid solution (25 ml), then with water (25 ml) and finally with brine (25 ml). The organic layer was dried over Na2SO4, filtered and concentrated. The resulting oil was finally purified by silica-gel column chromatography using Acetone/DCM system and desired compound was eluted with 20% acetone in DCM) to give the desired product 3-[5-(2,4-dioxobicyclo[3.2.1]octane-3-carbonyl)-3-methyl-6-oxo-pyridazin-1-yl]-N,N-dimethyl-propanamide as an orange oil.

$^1$H NMR (400 MHz, CDCl3): 16.18 (1H, brs), 6.99 (1H, s), 4.42 (2H, q), 3.09 (1H, m), 2.98 (3H, s), 2.93 (3H, s), 2.91 (1H, m), 2.80 (2H, t), 2.32 (3H, s), 2.24-2.08 (3H, m), 2.07-1.95 (1H, m), 1.90-1.79 (1H, m), 1.71 (1H, dt).

Step 2. Preparation of Compound 1.012

To 3-[5-(2,4-dioxobicyclo[3.2.1]octane-3-carbonyl)-3-methyl-6-oxo-pyridazin-1-yl]-N,N-dimethyl-propanamide (135 mg, 0.362 mmol) was added 2.0 mL acetonitrile and 2 ml water, then added 0.31 ml NaOH solution (1 M in water, 0.31 mmol) and stirred for 15 min at room temperature. The reaction mixture was then washed with DCM (10 ml) and the aqueous layer was lyophilized on a freeze-dryer. After lyophilisation, sodium 3-[2-[3-(dimethylamino)-3-oxo-propyl]-6-methyl-3-oxo-pyridazine-4-carbonyl]-4-oxo-bicyclo[3.2.1]oct-2-en-2-olate was afforded as a yellow solid.

$^1$H NMR (400 MHz, D2O) δ=7.06 (1H, s), 4.39 (2H, s), 3.05 (3H, s), 2.95 (3H, s), 2.92 (2H, t), 2.78 (2H, m), 2.36 (3H, s), 2.12-2.08 (3H, m), 1.74-1.72 (2H, m), 1.64-1.61 (1H, m)

PREPARATIVE EXAMPLE 5 (COMPOUND 1.017)

Step 1. Preparation of Sodium 2-[2-[4-(dimethylamino)-4-oxo-butyl]-6-methyl-3-oxo-pyridazine-4-carbonyl]-3-oxo-cyclohexen-1-olate To a solution of ethyl 3-methyl-6-oxo-1H-pyridazine-5-carboxylate (0.95 g, 5.21 mmol) and triphenylphosphine (1.78 g, 6.78 mmol) in tetrahydrofuran (anhydrous, 19 mL) under nitrogen was added 4-hydroxy-N,N-dimethyl-butanamide (0.89 g, 6.78 mmol). The solution was cooled to 0° C. and DIAD (1.37 g, 1.34 mL, 6.78 mmol) was added dropwise. The reaction mixture was stirred at 0° C. for 10 minutes and then at room temperature for 18 hours. The THF was removed in vacuo and the residue dissolved in DCM and washed with 2M HCl then brine. The organic phase was dried over magnesium sulfate, filtered and then concentrated to a thick yellow gum. To this was added iso-hexane (45 mL) and scratching was carried out until precipitation of a white solid occurred. The solid was filtered off, washing with more iso-hexane. The organic filtrate was concentrated to a yellow gum and then adsorbed onto silica and purified by automated column chromatography (40 g silica cartridge, 0 to 10% methanol in DCM). The sample was purified further by preparative HPLC to give ethyl 2-[4-(dimethylamino)-4-oxo-butyl]-6-methyl-3-oxo-pyridazine-4-carboxylate as a colourless gum.

$^1$H NMR (400 MHz, Chloroform) δ=7.59 (s, 1H), 4.38 (q, J=7.1 Hz, 2H), 4.23 (t, J=7.0 Hz, 2H), 2.99 (s, 3H), 2.94 (s, 3H), 2.41-2.36 (m, 2H), 2.36 (s, 3H), 2.15 (quin, J=7.2 Hz, 2H), 1.37 (t, J=7.2 Hz, 3H).

Step 2. Preparation of 2-[4-(dimethylamino)-4-oxo-butyl]-6-methyl-3-oxo-pyridazine-4-carboxylic Acid To a solution of ethyl 2-[4-(dimethylamino)-4-oxo-butyl]-6-methyl-3-oxo-pyridazine-4-carboxylate (0.670 g, 2.27 mmol) in tetrahydrofuran (17 mL) was added water (4 mL) and then lithium hydroxide hydrate (0.0952 g, 2.27 mmol). The resultant solution was stirred at room temperature for 35 minutes. The THF was then removed in vacuo and to the aqueous mixture was added DCM (20 mL) and 2M HCl (10 mL). The mixture was stirred vigorously for 5 minutes and then the organic phase collected through a phase separation cartridge and concentrated in vacuo to afford 2-[4-(dimethylamino)-4-oxo-butyl]-6-methyl-3-oxo-pyridazine-4-carboxylic acid as a white solid.

¹H NMR (400 MHz, Chloroform) δ=14.26 (br. s, 1H), 8.06 (s, 1H), 4.34 (t, 2H), 3.00 (s, 3H), 2.95 (s, 3H), 2.47 (s, 3H), 2.45-2.38 (m, 2H), 2.21 (quin, 2H).

Step 3. Preparation of Sodium 2-[2-[4-(dimethylamino)-4-oxo-butyl]-6-methyl-3-oxo-pyridazine-4-carbonyl]-3-oxo-cyclohexen-1-olate To a stirring suspension of 2-[4-(dimethylamino)-4-oxo-butyl]-6-methyl-3-oxo-pyridazine-4-carboxylic acid (0.390 g, 1.46 mmol) in 1,4-dioxane (5.85 mL) was added 1,1'-carbonyldiimidazole (0.355 g, 2.19 mmol) portion wise. The yellow solution was heated to 60° C. for 4 h 10 min. The mixture was cooled to room temperature and concentrated in vacuo to afford a yellow gum. This was cooled in an ice bath and DCM (10 mL) and ice-cooled water (10 mL) added and the mixture was stirred vigorously for 5 min. The mixture was allowed to attain room temperature and then the phases were separated. The organic phase was dried over magnesium sulfate, filtered and concentrated in vacuo to afford a yellow gum which was stored under nitrogen in the freezer overnight. The material was dissolved in dichloromethane (5.85 mL), put under nitrogen atmosphere and cooled in an ice bath. To it was added cyclohexane-1,3-dione (0.164 g, 1.46 mmol) in one portion followed by triethylamine (0.81 mL, 5.84 mmol). The mixture was stirred at 0° C. for 5 minutes and then for 2 h 15 min at room temperature. After this time, acetone cyanohydrin (0.0333 mL, 0.365 mmol) was added and the mixture heated at 40° C. for 1 h 15 min to afford a dark orange solution. The reaction mixture was cooled to room temperature, diluted with water and acidified to pH 1 with 2M HCl. Phases were separated and the aqueous phase was extracted into DCM (×2). The combined organic phases were washed with brine, dried over magnesium sulfate, filtered and concentrated in vacuo to afford a yellow gum. This was adsorbed onto silica then purified by automated column chromatography (24 g silica cartridge, 100% [20:8:4:4:1 toluene:1,4-dioxane:triethylamine:ethanol:water] for 15 minutes, then 0-20% EtOH in [20:8:4:4:1 toluene:1,4-dioxane:triethylamine:ethanol:water] over 15 minutes) to afford an orange gum. To this was added 2M HCl (10 mL) and DCM (10 mL) and mixture was stirred for 5 minutes. The phases were separated through a phase separation cartridge, washing with DCM. The organic phase was concentrated to afford 4-[5-(2,6-dioxocyclohexanecarbonyl)-3-methyl-6-oxo-pyridazin-1-yl]-N,N-dimethyl-butanamide as a yellow gum.

¹H NMR (400 MHz, Chloroform) δ=7.01 (s, 1H), 4.19 (t, 2H), 3.71 (s, 1H), 2.98 (s, 3H), 2.94 (s, 3H), 2.74 (br s, 2H), 2.46 (br d, 2H), 2.42-2.30 (m, 5H), 2.23-2.11 (m, 2H), 2.11-2.02 (m, 2H).

Step 4. Preparation of Compound 1.017

4-[5-(2,6-dioxocyclohexanecarbonyl)-3-methyl-6-oxo-pyridazin-1-yl]-N,N-dimethyl-butanamide (0.190 g, 0.526 mmol) was suspended in acetonitrile (1.14 mL) and 1M aq. sodium hydroxide (0.526 mL, 0.526 mmol) was added. After 10 minutes of stirring, the solution was freeze-dried (18 hours) to afford sodium 2-[2-[4-(dimethylamino)-4-oxo-butyl]-6-methyl-3-oxo-pyridazine-4-carbonyl]-3-oxo-cyclohexen-1-olate (0.18 g, 0.4695 mmol) as an orange solid.

¹H NMR (400 MHz, DMSO-d₆) δ=6.51 (s, 1H), 3.93 (t, J=6.7 Hz, 2H), 2.91 (s, 3H), 2.80 (s, 3H), 2.30 (t, J=7.4 Hz, 2H), 2.16 (s, 3H), 2.14-2.07 (m, 4H), 1.85 (t, J=7.2 Hz, 2H), 1.73-1.65 (m, 2H).

TABLE 1

Examples of herbicidal compounds of the present invention.

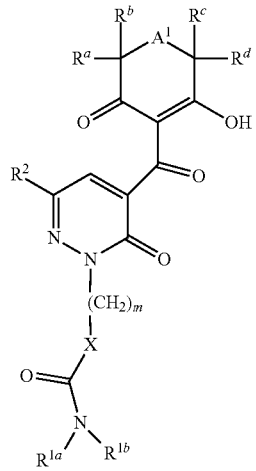

(I)

| Compound Number | R¹ᵃ | R¹ᵇ | R² | X | A¹ | Rᵇ | Rᵃ | Rᶜ | Rᵈ | m |
|---|---|---|---|---|---|---|---|---|---|---|
| 1.001 | Me | Me | Me | CH₂ | CH₂ | H | H | H | H | 0 |
| 1.002 | Me | Me | Me | CH₂ | CH₂ | H | H | H | H | 1 |
| 1.003 | —CH₂CH₂OCH₂CH₂— | | Me | CH₂ | CH₂ | H | H | H | H | 0 |
| 1.004 | —CH₂CH₂OCH₂CH₂— | | Me | CH₂ | CH₂ | H | H | H | H | 1 |
| 1.005 | —CH₂CH₂CH₂CH₂— | | Me | CH₂ | CH₂ | H | H | H | H | 1 |
| 1.006 | Me | H | Me | CH₂ | CH₂ | H | H | H | H | 1 |
| 1.007 | Et | Et | Me | CH₂ | CH₂ | H | H | H | H | 1 |
| 1.008 | Me | H | Me | O | CH₂ | H | H | H | H | 2 |

TABLE 1-continued

Examples of herbicidal compounds of the present invention.

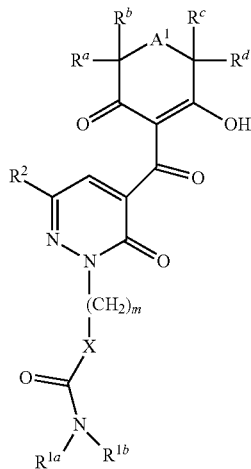

(I)

| Compound Number | $R^{1a}$ | $R^{1b}$ | $R^2$ | X | $A^1$ | $R^b$ | $R^a$ | $R^c$ | $R^d$ | m |
|---|---|---|---|---|---|---|---|---|---|---|
| 1.009 | Me | Me | Me | O | $CH_2$ | H | H | H | H | 2 |
| 1.010* | Me | Me | Me | $CH_2$ | $CH(CH_3)$ | H | H | H | H | 1 |
| 1.011* | Me | Me | Me | $CH_2$ | $C(CH_3)_2$ | H | H | H | H | 1 |
| 1.012* | Me | Me | Me | $CH_2$ | $CH_2$ | H | —$CH_2CH_2$— | H | 1 |
| 1.013* | Me | Et | Me | $CH_2$ | $CH_2$ | H | H | H | H | 1 |
| 1.014* | $CF_3CH_2$— | Me | Me | $CH_2$ | $CH_2$ | H | H | H | H | 1 |
| 1.015* | Me | Me | Me | O | $CH_2$ | H | H | H | H | 2 |
| 1.016* | Me | Me | cPr | $CH_2$ | $CH_2$ | H | H | H | H | 1 |
| 1.017* | Me | Me | Me | $CH_2$ | $CH_2$ | H | H | H | H | 2 |
| 1.018* | Me | Me | Me | $CF_2$ | $CH_2$ | H | H | H | H | 1 |
| 1.019 | Me | MeO— | Me | $CH_2$ | $CH_2$ | H | H | H | H | 1 |
| 1.020* | Me | $CF_3CH_2$ | Me | $CH_2$ | $CH(CH_3)$ | H | H | H | H | 1 |
| 1.021* | Et | Et | Me | O | $CH_2$ | H | H | H | H | 2 |
| 1.022* | Me | Et | Me | O | $CH_2$ | H | H | H | H | 2 |
| 1.023* | Me | $CF_3CH_2$ | Me | O | $CH_2$ | H | H | H | H | 2 |
| 1.024* | —$CH_2CH_2CH_2CH_2$— | | Me | O | $CH_2$ | H | H | H | H | 2 |
| 1.025* | —$CH_2CH_2OCH_2CH_2$— | | Me | O | CH2 | H | H | H | H | 2 |
| 1.026* | Me | Me | Me | O | $CH(CH_3)$ | H | H | H | H | 2 |
| 1.027* | Me | Me | Me | O | $C(CH_3)_2$ | H | H | H | H | 2 |
| 1.028* | Me | Me | Me | $CH(CH_3)$ | $CH_2$ | H | H | H | H | 0 |
| 1.029* | Me | Me | Me | $CH(CH_3)$ | $CH_2$ | H | H | H | H | 0 |

*provided as the sodium salt.

TABLE 2

NMR information.

| Compound Number | $^1$H NMR (400 MHz, Chloroform - unless otherwise stated). |
|---|---|
| 1.001 | δ 16.08 (1H, brs), 7.09 (1H, s), 4.90 (2H, s), 3.03 (3H, s), 2.95 (3H, s), 2.70 (2H, m), 2.46 (2H, m), 2.35 (3H, s), 2.05 (2H, m). |
| 1.002 | δ 16.18 (1H, brs), 7.00 (1H, s), 4.41 (2H, t), 2.98 (3H, s), 2.93 (3H, s), 2.79 (2H, t), 2.72 (2H, t), 2.45 (2H, t), 2.32 (3H, s), 2.05 (2H, quintet) |
| 1.003 | δ = 16.11 (1H, s), 7.08 (1H, s), 4.90 (1H, s), 3.68 (4H, m), 3.61 (2H, m), 3.47 (2H, m), 2.71 (2H, m), 2.45 (2H, m), 2.35 (3H, s), 2.04 (2H, m). |
| 1.004 | δ = 16.20 (1H, s), 7.01 (1H, s), 4.42 (2H, t), 3.64-3.60 (6H, m), 3.45 (2H, m), 2.80 (2H, t), 2.73 (2H, t), 2.45 (2H, t), 2.33 (3H, s), 2.08-2.02 (2H, m). |
| 1.005 | δ = 16.18 (1H, s), 7.00 (1H, s), 4.43 (2H, t), 3.45 (2H, t), 3.40 (2H, t), 2.76-2.70 (4H, m), 2.46 (2H, t), 2.32 (3H, s), 2.08-2.02 (2H, m), 1.95-1.88 (2H, m), 1.86-1.79 (2H, m) |
| 1.006 | δ = 16.24 (1H, brs), 7.02 (1H, s), 6.55 (1H, brs), 4.40 (2H, m), 2.74 (2H, t), 2.70 (3H, d), 2.64 (2H, t), 2.46 (2H, t), 2.32 (3H, s), 2.06 (2H, m) |
| 1.007 | δ = 16.17 (1H, s), 7.01 (1H, s), 4.43 (2H, t), 3.36 (2H, q), 3.27 (2H, q), 2.78 (2H, t), 2.72 (2H, t), 2.46 (2H, t), 2.33 (3H, s), 2.05 (2H, m), 1.14 (3H, t), 1.09 (3H, t) |
| 1.008 | δ = 7.05 (s, 1H), 5.48 (br. s., 1H), 4.40 (br. s., 4H), 2.82-2.65 (m, 5H), 2.48 (t, J = 6.2 Hz, 2H), 2.35 (s, 3H), 2.14-2.01 (m, 2H) |
| 1.009 | δ = 7.02 (s, 1H), 4.46-4.28 (m, 4H), 2.95-2.80 (m, 6H), 2.73 (br. s, 2H), 2.48 (br. s, 2H), 2.34 (s, 3H), 2.06 (quin, J = 6.4 Hz, 2H) |

TABLE 2-continued

NMR information.

| Compound Number | $^{1}$H NMR (400 MHz, Chloroform - unless otherwise stated). |
|---|---|
| 1.010 | 1H NMR (400 MHz, D$_2$O) δ = 7.10 (1H, s), 4.39 (2H, t), 3.05 (3H, s), 2.95 (3H, s), 2.92 (2H, t), 2.49-2.46 (2H, m), 2.36 (3H, s), 2.26-2.18 (3H, m), 1.04 (3H, s) |
| 1.011 | 1H NMR (400 MHz, D$_2$O) δ = 7.09 (1H, s), 4.39 (2H, t), 3.05 (3H, s), 2.95 (3H, s), 2.92 (2H, t), 2.36 (3H, s), 2.34 (4H, s), 1.06 (6H, s) |
| 1.012 | 1H NMR (400 MHz, D$_2$O) δ = 7.06 (1H, s), 4.39 (2H, s), 3.05 (3H, s), 2.95 (3H, s), 2.92 (2H, t), 2.78 (2H, m), 2.36 (3H, s), 2.12-2.08 (3H, m), 1.74-1.72 (2H, m), 1.64-1.61 (1H, m) |
| 1.013 | 1H NMR (400 MHz, DMSO-d6): Mixture of rotamers seen: 6.67 (1H, s), 4.11-4.09 (2H, m), 3.31-3.29 (4H, m), 2.90 (1.5 H, s), 2.79 (1.5 H, s), 2.68-2.64 (2H, m), 2.22-2.16 (7H, m), 1.75-1.72 (2H, m), 1.10-1.06 (1.5H, m), 1.01-0.97 (1.5H, m). |
| 1.014 | (1H NMR (400 MHz, DMSO-d6): 6.62 (1H, s), 4.32-4.11 (4H, m), 3.06 (3H, s), 2.80-2.76 (2H, m), 2.20-2.15 (7H, m), 1.74-1.71 (2H, m) |
| 1.015 | 1H NMR (400 MHz, DMSO-d6) δ = 6.58 (d, 1H), 4.24-4.11 (m, 4H), 2.82-2.73 (m, 6H), 2.23-2.11 (m, 7H), 1.78-1.66 (m, 2H) |
| 1.016 | δ = 6.61 (1H, s), 4.35 (2H, m), 2.96 (3H, s), 2.90 (3H, s), 2.82 (2H, m), 2.24 (4H, m), 1.82-1.73 (3H, m), 0.90-0.86 (2H, m), 0.78-0.75 (2H, m) |
| 1.017 | 1H NMR (400 MHz, DMSO-d6) δ = 6.51 (s, 1H), 3.93 (t, 2H), 2.91 (s, 3H), 2.80 (s, 3H), 2.30 (t, 2H), 2.16 (s, 3H), 2.14-2.07 (m, 4H), 1.85 (t, 2H), 1.73-1.65 (m, 2H) |
| 1.018 | 1H NMR (400 MHz, DMSO-d6) δ = 6.57 (s, 1H), 6.53 (s, 0.23H), 4.63 (t, J = 15.2 Hz, 2H), 4.41 (br t, J = 16.0 Hz, 0.54H), 3.07 (s, 3H), 2.91 (s, 3H), 2.23-2.07 (m, 9H), 1.75-1.67 (m, 2.5H) |
| 1.020 | (DMSO-d6): 6.58(s, 1H), 4.36-4.07(m, 4H), 3.07(s, 2H), 2.92(s, 1H), 2.82-2.71(m, 2H), 2.20-2.13(m, 5H), 2.02-1.85(m, 3H), 0.93(d, 3H) |
| 1.021 | 1H NMR (400 MHz, D$_2$O) δ = 7.12 (1H, s), 4.45-4.43 (4H, m), 3.24 (4H, q), 2.43-2.40 (4H, m), 2.37 (3H, s), 1.94-1.91 (2H, m) |
| 1.022 | 1H NMR (400 MHz, D$_2$O) δ = 6.96 (1H, s), 4.29-4.26 (4H, m), 3.10 (2H, q), 2.69 (3H, s), 2.28-2.25 (4H, m), 2.21 (3H, s), 1.78-1.75 (2H, m) |
| 1.023 | 1H NMR (400 MHz, D$_2$O) δ = 7.11 (1H, s), 4.50 (2H, m), 4.26 (2H, m), 2.38 (2H, m), 2.99 (3H, s), 2.43-2.40 (4H, m), 2.36 (3H, s), 1.94-1.91 (2H, m) |
| 1.024 | 1H NMR (400 MHz, D$_2$O) δ = 7.10 (1H, s), 4.46-4.40 (4H, m), 3.28 (4H, brs), 2.42 (4H, m), 2.36 (3H, s), 1.92-1.87 (6H, m) |
| 1.025 | (1H NMR (400 MHz, D$_2$O) δ = 7.09 (1H, s), 4.50-4.41 (4H, m), 3.69 (4H, brs), 3.45 (4H, brs), 2.43-2.40 (4H, m), 2.37 (3H, s), 1.94-1.91 (2H, m) |
| 1.026 | (1H NMR (400 MHz, D$_2$O) δ = 7.10 (1H, s), 4.46-4.41 (4H, m), 2.87 (6H, s), 2.50-2.47 (2H, m), 2.37 (3H, s), 2.21-2.19 (3H, m), 1.05 (3H, d), |
| 1.027 | 1H NMR (400 MHz, D$_2$O) δ = 7.09 (1H, s), 4.46-4.40 (4H, m), 2.87 (6H, s), 2.32 (3H, s), 2.34 (4H, s), 1.07 (6H, s). |
| 1.029 | (CDCl3): 7.33 (1H, q), 6.63 (1H, s), 2.90 (3H, s), 2.85 (3H, s), 2.30-2.23 (7H, m), 1.84-1.75 (2H, m), 1.62 (3H, d) |

BIOLOGICAL EXAMPLES

Seeds of a variety of test species were sown in standard soil in pots (*Amaranthus* retoflexus (AMARE), *Abutilon theophrasti* (ABUTH), *Digitaria sanguinalis* (DIGSA), *Setaria faberi* (SETFA) and *Zea mays* (ZEAMX). After cultivation for 10 days under controlled conditions in a glasshouse (at 24/16° C., day/night; 14 hours light; 65% humidity), the plants were sprayed with an aqueous spray solution derived from the formulation of the technical active ingredient in 0.6 ml acetone and 45 ml formulation solution containing 10.6% Emulsogen EL (Registry number 61791-12-6), 42.2% N-methyl pyrrolidone, 42.2% dipropylene glycol monomethyl ether (CAS RN 34590-94-8) and 0.2% X-77 (CAS RN 11097-66-8). The test plants were then grown in a glasshouse under controlled conditions in a glasshouse (at 24/16° C., day/night; 14 hours light; 65% humidity) and watered twice daily. After 14 days the test is evaluated for the percentage damage caused to the plant. The biological activities are shown in the following table on a five point scale (5=80-100%; 4=60-79%; 3=40-59%; 2=20-39%; 1=0-19%).

TABLE B1

| | POST Application (125 g/ha) | | | | |
|---|---|---|---|---|---|
| Compound | AMARE | ABUTH | DIGSA | SETFA | ZEAMX |
| 1.001 | 5 | 5 | 5 | 5 | 1 |
| 1.002 | 5 | 5 | 5 | 5 | 1 |
| 1.004 | 5 | 5 | 5 | 5 | 1 |
| 1.006 | 5 | 4 | 5 | 5 | 1 |
| 1.007 | 5 | 5 | 5 | 5 | 1 |
| 1.008 | 5 | 5 | 5 | 5 | 1 |
| 1.009 | 5 | 5 | 5 | 4 | 1 |
| 1.010 | 5 | 5 | 5 | 5 | 1 |
| 1.013 | 5 | 5 | 5 | 5 | 1 |
| 1.014 | 5 | 5 | 5 | 5 | 1 |
| 1.016 | 5 | 5 | 5 | 4 | 1 |

TABLE B1-continued

| | POST Application (125 g/ha) | | | | |
|---|---|---|---|---|---|
| Compound | AMARE | ABUTH | DIGSA | SETFA | ZEAMX |
| 1.018 | 5 | 5 | 5 | 5 | 1 |
| 1.020 | 4 | 5 | 5 | 5 | 1 |
| 1.021 | 4 | 5 | 5 | 5 | 1 |
| 1.022 | 5 | 5 | 5 | 5 | 1 |
| 1.023 | 3 | 3 | 5 | 5 | 1 |
| 1.024 | 4 | 2 | 5 | 5 | 1 |
| 1.025 | 5 | 5 | 5 | 5 | 1 |
| 1.026 | 5 | 5 | 5 | 5 | 1 |
| 1.027 | 5 | 5 | 5 | 5 | 1 |
| 1.029 | 5 | 5 | 5 | 5 | 1 |
| Compound 1.2 WO2012/136793 | 5 | 5 | 5 | 5 | 3 |

These data show that the compounds of the present invention provide unexpectedly improved crop selectivity in corn (*Zea mays*) compared to the compounds disclosed in WO 2012/136703 whilst delivering comparable weed control.

The invention claimed is:

1. A compound of Formula (I):

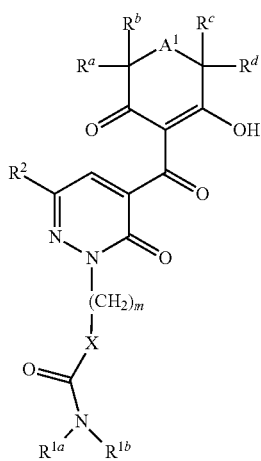

(I)

or an agronomically acceptable salt thereof,
wherein:
$R^{1a}$ is selected from the group consisting of hydrogen, $C_1$-$C_6$alkyl and $C_1$-$C_6$haloalkyl;
$R^{1b}$ is selected from the group consisting of hydrogen, $C_1$-$C_6$alkyl, $C_1$-$C_3$alkoxy- and $C_1$-$C_6$haloalkyl; or
$R^{1a}$ and $R^{1b}$ together are —CH$_2$CH$_2$CH$_2$CH$_2$—, —CH$_2$CH$_2$CH$_2$CH$_2$CH$_2$— or —CH$_2$CH$_2$OCH$_2$CH$_2$—; and
X is selected from the group consisting of O, —CF$_2$—, —C(CH$_3$)— and —CH$_2$—;
m is 0, 1 or 2 wherein if X is O or —CF$_2$— then m is 1 or 2;
$R^2$ is selected from the group consisting of hydrogen, $C_1$-$C_6$alkyl and $C_3$-$C_6$cycloalkyl;
$A^1$ is selected from the group consisting of O, C(O) and (CR$^e$R$^f$); and
$R^a$, $R^b$, $R^c$, $R^d$, $R^e$ and $R^f$ are each independently selected from the group consisting of hydrogen and $C_1$-$C_4$alkyl wherein $R^a$ and $R^c$ may together form a $C_1$-$C_3$alkylene chain.

2. The compound according to claim 1, wherein X is selected from the group consisting of O, —CF$_2$— and —CH$_2$—.

3. The compound according to claim 1, wherein X is O.

4. The compound according to claim 1, wherein X is —CH$_2$—.

5. The compound according to claim 1, wherein $R^2$ is methyl.

6. The compound according to claim 1, wherein $R^{1a}$ and $R^{1b}$ are both $C_1$-$C_6$alkyl.

7. The compound according to claim 1, wherein $A^1$ is (CR$^e$R$^f$).

8. The compound according to claim 1, wherein $R^a$, $R^b$, $R^c$, $R^d$, $R^e$ and $R^f$ are hydrogen.

9. A compound according to claim 1, wherein $R^a$, $R^b$, $R^c$, $R^d$, $R^e$ are hydrogen and $R^f$ is methyl.

10. A herbicidal composition comprising a compound according to claim 1 and an agriculturally acceptable formulation adjuvant.

11. The herbicidal composition according to claim 10, further comprising at least one pesticide.

12. The herbicidal composition according to claim 11, wherein the pesticide is a herbicide or herbicide safener.

13. A method of controlling weeds at a locus, comprising: applying a weed controlling amount of a composition according to claim 10 to the locus of a weed.

14. A compound of Formula (IV):

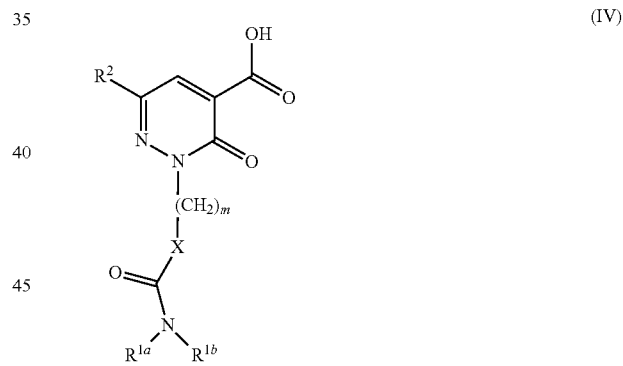

(IV)

wherein
$R^{1a}$ is selected from the group consisting of hydrogen, $C_1$-$C_6$alkyl and $C_1$-$C_6$haloalkyl;
$R^{1b}$ is selected from the group consisting of hydrogen, $C_1$-$C_6$alkyl, $C_1$-$C_3$alkoxy- and $C_1$-$C_6$haloalkyl; or
$R^{1a}$ and $R^{1b}$ together are —CH$_2$CH$_2$CH$_2$CH$_2$—, —CH$_2$CH$_2$CH$_2$CH$_2$CH$_2$— or —CH$_2$CH$_2$OCH$_2$CH$_2$—; and
X is selected from the group consisting of O, —CF$_2$—, —C(CH$_3$)— and —CH$_2$—;
m is 0, 1 or 2 wherein if X is O or —CF$_2$— then m is 1 or 2;
$R^2$ is selected from the group consisting of hydrogen, $C_1$-$C_6$alkyl and $C_3$-$C_6$cycloalkyl.

15. A compound of formula (I)

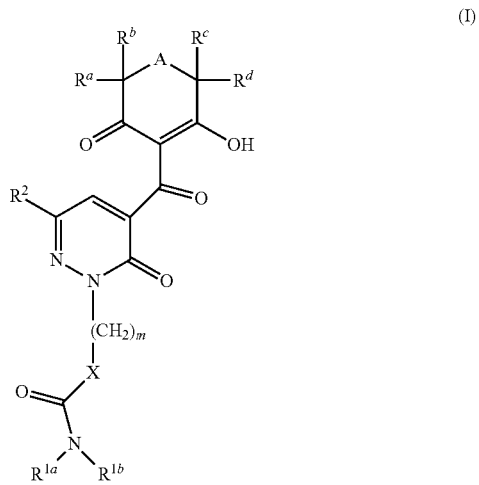

wherein $R^{1a}$, $R^{1b}$, $R^2$, X, A, $R^b$, $R^a$, $R^c$, $R^d$, and m are defined as follows:

| $R^{1a}$ | $R^{1b}$ | $R^2$ | X | $A = A^1$ | $R^b$ | $R^a$ | $R^c$ | $R^d$ | m |
|---|---|---|---|---|---|---|---|---|---|
| Me | Me | Me | $CH_2$ | $CH_2$ | H | H | H | H | 0 |
| Me | Me | Me | $CH_2$ | $CH_2$ | H | H | H | H | 1 |
| —$CH_2CH_2OCH_2CH_2$— | | Me | $CH_2$ | $CH_2$ | H | H | H | H | 0 |
| —$CH_2CH_2OCH_2CH_2$— | | Me | $CH_2$ | $CH_2$ | H | H | H | H | 1 |
| —$CH_2CH_2CH_2CH_2$— | | Me | $CH_2$ | $CH_2$ | H | H | H | H | 1 |
| Me | H | Me | $CH_2$ | $CH_2$ | H | H | H | H | 1 |
| Et | Et | Me | $CH_2$ | $CH_2$ | H | H | H | H | 1 |
| Me | H | Me | O | $CH_2$ | H | H | H | H | 2 |
| Me | Me | Me | O | $CH_2$ | H | H | H | H | 2 |
| Me | Me | Me | $CH_2$ | $CH(CH_3)$ | H | H | H | H | 1 |
| Me | Me | Me | $CH_2$ | $C(CH_3)_2$ | H | H | H | H | 1 |
| Me | Me | Me | $CH_2$ | $CH_2$ | H | —$CH_2CH_2$— | | H | 1 |
| Me | Et | Me | $CH_2$ | $CH_2$ | H | H | H | H | 1 |
| $CF_3CH_2$— | Me | Me | $CH_2$ | $CH_2$ | H | H | H | H | 1 |
| Me | Me | Me | O | $CH_2$ | H | H | H | H | 2 |
| Me | Me | cPr | $CH_2$ | $CH_2$ | H | H | H | H | 1 |
| Me | Me | Me | $CH_2$ | $CH_2$ | H | H | H | H | 2 |
| Me | Me | Me | $CF_2$ | $CH_2$ | H | H | H | H | 1 |
| Me | MeO— | Me | $CH_2$ | $CH_2$ | H | H | H | H | 1 |
| Me | $CF_3CH_2$ | Me | $CH_2$ | $CH(CH_3)$ | H | H | H | H | 1 |
| Et | Et | Me | O | $CH_2$ | H | H | H | H | 2 |
| Me | Et | Me | O | $CH_2$ | H | H | H | H | 2 |
| Me | $CF_3CH_2$ | Me | O | $CH_2$ | H | H | H | H | 2 |
| —$CH_2CH_2CH_2CH_2$— | | Me | O | $CH_2$ | H | H | H | H | 2 |
| —$CH_2CH_2OCH_2CH_2$— | | Me | O | $CH_2$ | H | H | H | H | 2 |
| Me | Me | Me | O | $CH(CH_3)$ | H | H | H | H | 2 |
| Me | Me | Me | O | $C(CH_3)_2$ | H | H | H | H | 2 |
| Me | Me | Me | $CH(CH_3)$ | $CH_2$ | H | H | H | H | 0 |
| Me | Me | Me | $CH(CH_3)$ | $CH_2$ | H | H | H | H | 0 |

* * * * *